United States Patent
Lal et al.

(10) Patent No.: US 6,808,895 B1
(45) Date of Patent: Oct. 26, 2004

(54) DNA ENCODING OXIDOREDUCTASE AND POLYPEPTIDE ENCODED THEREBY

(75) Inventors: Preeti Lal, Santa Clara, CA (US); Karl J. Guegler, Menlo Park, CA (US); Gina A. Gorgone, Boulder Creek, CA (US); Neil C. Corley, Castro Valley, CA (US); Mariah R. Baughn, San Leandro, CA (US); Y. Tom Tang, San Jose, CA (US); Jennifer L. Hillman, Mountain View, CA (US); Olga Bandman, Mountain View, CA (US); Yalda Azimzai, Castro Valley, CA (US); Janice Au-Young, Brisbane, CA (US); Henry Yue, Sunnyvale, CA (US); Dyung Aina M. Lu, San Jose, CA (US); Junming Yang, San Jose, CA (US)

(73) Assignee: Incyte Corporation, Palo Alto, CA (US)

( * ) Notice: Subject to any disclaimer, the term of this patent is extended or adjusted under 35 U.S.C. 154(b) by 0 days.

(21) Appl. No.: 09/806,536

(22) PCT Filed: Oct. 6, 1999

(86) PCT No.: PCT/US99/23434

§ 371 (c)(1),
(2), (4) Date: Mar. 28, 2001

(87) PCT Pub. No.: WO00/20604

PCT Pub. Date: Apr. 13, 2000

(51) Int. Cl.[7] .............................. C12N 5/10; C12N 9/02; C12N 15/52; C12N 15/63; G01N 33/53
(52) U.S. Cl. .................... 435/69.1; 536/23.2; 536/24.3; 536/24.31; 530/350; 435/71.1; 435/71.2; 435/471; 435/325; 435/252.3; 435/254.11; 435/320.1; 435/6; 435/7.1
(58) Field of Search ............................ 435/6, 7.1, 69.1, 435/71.1, 71.2, 671, 325, 252.3, 254.11, 320.1; 536/23.2, 24.3, 24.31; 530/30

(56) References Cited

U.S. PATENT DOCUMENTS 6,100,075 A 8/2000 Hillman et al.
6,268,192 B1 7/2001 Hillman et al.

FOREIGN PATENT DOCUMENTS

WO   WO 99/14328      3/1999
WO   WO 99/38881      8/1999
WO   WO 02/099043 A2  12/2002

OTHER PUBLICATIONS

Dougherty et al. (1992), The Journal of Biological Chemistry, vol. 267, No. 2, pp. 871–875.*
Reiger et al. (1996) Glossary of Genetics and Cytogenetics, 4th edition, Springer–Verlag, pp. 16–19.*
Merrill, M.J. et al., "Purification Human Erythrocyte Pyrroline–5–carboxylate Reductase", *J. Biol. Chem.*, 264(16):9352–9358 (1989).
Isogai, T. et al., NCBI Database, Accession AK023914 (GI 10435995), Aug. 1, 2002.
Strausberg, R., NCBI Database, Accession BC007993 (GI 14124939), Jul. 12, 2001.
Strausberg, R., NCBI Database, Accession BC026536 (GI 20071633), Sep. 20, 2002.
Strausberg, R., NCBI Database, Accession BC001504 (GI 16306657), Oct. 29, 2001.
Ansorge, W. et al., NCBI Database, Accession AL833857 (GI 21739340), Jul. 12, 2002.
Carninci, P. and Y. Hayashizaki, NCBI Database, Accession AK002912 (GI 12833244), Dec. 5, 2002.
Carninci, P. and Y. Hayashizaki, NCBI Database, Accession AK004291 (GI 12835422), Dec. 5, 2002.
NCBI Database, Accession CAA91943 (GI 3878731), May 21, 2003.
Willett, C.S. and R.S. Burton, NCBI Database, Accession AF512515 (GI 21327262), Jul. 24, 2002.
Dougherty, K.M. et al., NCBI Database, Accession M77836 (GI 189497) Apr. 27, 1993.
Blum, H. et al., R61u001 Database Entry Hsm800581, Accession AL080080, Jun. 23, 1999.

* cited by examiner

*Primary Examiner*—Prema Mertz
(74) *Attorney, Agent, or Firm*—Incyte Corporation

(57) ABSTRACT

The invention provides human oxidoreductase molecules (OXRE) and polynucleotides which identify and encode OXRE. The invention also provides expression vectors, host cells, antibodies, agonists, and antagonists. The invention also provides methods for diagnosing, treating, or preventing disorders associated with expression of OXRE.

14 Claims, No Drawings

DNA ENCODING OXIDOREDUCTASE AND POLYPEPTIDE ENCODED THEREBY

TECHNICAL FIELD

This invention relates to nucleic acid and amino acid sequences of oxidoreductase molecules and to the use of these sequences in the diagnosis, treatment, and prevention of cell proliferative disorders including cancer, endocrine, metabolic, reproductive, neurological, autoimmune/inflammatory, and viral disorders.

BACKGROUND OF THE INVENTION

Many pathways of biogenesis and biodegradation require oxidoreductase (dehydrogenase or reductase) activity, coupled to the reduction or oxidation of a donor or acceptor cofactor. Potential cofactors include cyrochromes, oxygen, disulfide, iron-sulfur proteins, flavin adenine dinucleotide (FAD), and the nicotinamide adenine dinucleotides NAD and NADP (Newsholme, E. A. and Leech, A. R. (1983) *Biochemistry for the Medical Sciences*, John Wiley and Sons, Chichester, U. K. pp. 779–793).

Reductase activity catalyzes the transfer of electrons between substrate(s) and cofactor(s) with concurrent oxidation of the cofactor. The reverse dehydrogenase reaction catalyzes the reduction of a cofactor and consequent oxidation of the substrate. Oxidoreductase enzymes are a broad superfamily of proteins that catalyze numerous reactions in all cells of organisms ranging from bacteria to plants to humans. These reactions include metabolism of sugar, certain detoxification reactions in the liver, and the synthesis or degradation of fatty acids, amino acids, glucocorticoids, estrogens, androgens, and prostaglandins. Different family members are named according to the direction in which their reactions are typically catalyzed; thus they may be referred to as oxidoreductases, oxidases, reductases, or dehydrogenases. In addition, family members often have distinct cellular localizations, including the cytosol, the plasma membrane, mitochondrial inner or outer membrane, and peroxisomes.

Tetrahydrofolate is a derivatized glutamate molecule that acts as a carrier, providing activated one-carbon units to a wide variety of biosynthetic reactions, including synthesis of purines, pyrimidines, and the amino acid methionine. Tetrahydrofolate is generated by the activity of a holoenzyme complex called tetrahydrofolate synthase, which includes three enzyme activities: tetrahydrofolate dehydrogenase, tetrahydrofolate cyclohydrolase, and tetrahydrofolate synthetase. Thus, tetrahydrofolate dehydrogenase plays an important role in generating building blocks for nucleic and amino acids, crucial to proliferating cells.

Intracellular redox status plays a critical role in the assembly of proteins. A major rate limiting step in protein folding is the thiol:disulfide exchange necessary for correct protein assembly. Although incubation of reduced, unfolded proteins in buffers containing defined ratios of oxidized and reduced thiols can lead to folding into native conformation, the rate-of folding is slow, and the attainment of the native conformation decreases proportionately with protein size and the number of cysteine residues. Certain cellular compartments such as the endoplasmic reticulum of eukaryotes and the periplasmic space of prokaryotes are maintained in a more oxidized state than the surrounding cytosol. Correct disulfide formation can occur in these compartments, but it occurs at a rate that is insufficient for normal cell processes and inadequate for synthesizing secreted proteins.

Protein disulfide isomerases (PDIs), thioredoxins, and glutaredoxins are able to catalyze the formation of disulfide bonds and regulate the redox environment in cells to enable the necessary thiol:disulfide exchanges. Each of these classes of molecules has a somewhat different function, but all belong to a group of disulfide-containing redox proteins that contain a conserved active-site sequence and are ubiquitously distributed in eukaryotes and prokaryotes. PRIs are found in the endoplasmic reticulum of eukaryotes and in the periplasmic space of prokaryotes. PRIs function by exchanging their own disulfide for thiols in a folding peptide chain. In contrast, reduced thioredoxins and glutaredoxins are generally found in the cytoplasm and function by directly reducing disulfides in the substrate proteins. Thioredoxin (Trx), a heat-stable, redox-active protein, contains an active site cysteine disulfide/dithiol. Oxidized thioredoxin, Trx-S, can be reduced to the dithiol form by NADPH and a specific flavoprotein enzyme, thioredoxin reductase. Reduced thioredoxin, Trx-(SH), participates in a number of redox reactions mostly linked to reduction of protein disulfides. Trx and thioredoxin reductase (TR), together with NADPH, form a redox complex in which TR catalyzes the electron transport from NADPH to Trx. The reduced thioredoxin then functions as an electron donor in a wide variety of different metabolic processes.

Disulfide-containing redox proteins not only facilitate disulfide formation, but also regulate and participate in a wide variety of physiological processes. The thioredoxin system serves, for example, as a hydrogen donor for ribonucleotide reductase and controls the activity of enzymes by redox reactions. Mammalian thioredoxin (MT) acts as a hydrogen donor for ribonucleotide reductase and methionine sulfoxide reductase, facilitates refolding of disulfide-containing proteins, and activates the glucocorticoid and interleukin-2 receptors. MT also modulates the DNA binding activity of some transcription factors either directly (TFIIIC, BZLF1, and NF-kB) or indirectly (AP-1) through the nuclear factor Ref-1. The importance of the redox regulation of transcription factors is exemplified by the v-fos oncogene where a point mutation of the thioredoxin-modulated cysteine residue results in constitutive activation of the AP-1 complex. Thioredoxin is secreted by cells using a leaderless pathway and stimulates the proliferation of lymphoid cells, fibroblasts, and a variety of human solid tumor cell lines. Furthermore, thioredoxin is an essential component of early pregnancy factor, inhibits human immunodeficiency virus expression in macrophages, reduces $H_2O_2$, scavenges free radicals, and protects cells against oxidative stress (Abate, C. et al., (1990) Science 249: 1157–1161; Rosen, A. et al. (1995) Int. Immunol. 7: 625–633; Tagaya, Y. et al (1989) EMBO J. 8: 757–764; Newman, G. W. (1994) J. Expt. Med. 180: 359–363; and Makino, Y. (1996) J. Clin. Invest. 98: 2469–2477).

Short-chain alcohol dehydrogenases (SCADs) are a family of dehydrogenases that share only 15% to 30% sequence identity, with similarity predominantly in the coenzyme binding domain and the substrate binding domain. In addition to the well-known role in detoxification of ethanol, SCADs are also involved in synthesis and degradation of fatty acids, steroids, and some prostaglandins, and are therefore implicated in a variety of disorders such as lipid storage disease, myopathy, SCAD deficiency, and certain genetic disorders. For example, retinol dehydrogenase is a SCAD-family member (Simon, A. et al. (1995) J. Biol. Chem. 270:1107–1112) that converts retinol to retinal, the precursor of retinoic acid. Retinoic acid, a regulator of differentiation and apoptosis, has been shown to down-regulate genes involved in cell proliferation and inflammation (Chai, X. et al. (1995) J. Biol. Chem. 270:3900–3904). In addition, retinol dehydrogenase has been linked to hereditary eye diseases such as autosomal recessive childhood-onset severe retinal dystrophy (Simon, A. et al. (1996) Genomics 36:424–430).

Propagation of nerve impulses, modulation of cell proliferation and differentiation, induction of the immune response, and tissue homeostasis involve neurotransmitter metabolism (Weiss, B. (1991) Neurotoxicology 12:379–386; Collins, S. M. et al. (1992) Ann. N.Y. Acad. Sci. 664:415–424; Brown, J. K. and Imam, H. (1991) J. Inherit. Metab. Dis. 14:436–458). Many pathways of neurotransmitter metabolism require oxidoreductase activity, coupled to reduction or oxidation of a cofactor, such as $NAD^+/NADH$ (Newsholme, E. A. and Leech, A. R. (1983) *Biochemistry for the Medical Sciences*, John Wiley and Sons, Chichester, U.K. pp. 779–793). Degradation of catecholamines (epinephrine or norepinephrine) requires alcohol dehydrogenase (in the brain) or aldehyde dehydrogenase (in peripheral tissue). $NAD^+$-dependent aldehyde dehydrogenase oxidizes 5-hydroxyindole-3-acetate (the product of 5-hydroxytryptamine (serotonin) metabolism) in the brain, blood platelets, liver and pulmonary endothelium (Newsholme, E. A. and Leech, A. R. (supra) p. 786). Other neurotransmitter degradation pathways that utilize $NAD^+/NADH$-dependent oxidoreductase activity include those of L-DOPA (precursor of dopamine, a neuronal excitatory compound), glycine (an inhibitory neurotransmitter in the brain and spinal cord), histamine (liberated from mast cells during the inflammatory response), and taurine (an inhibitory neurotransmitter of the brain stem, spinal cord and retina) (Newsholme, E. A. and Leech, A. R. supra. pp.790, 792). Epigenetic or genetic defects in neurotransmitter metabolic pathways can result in a spectrum of disease states in different tissues including Parkinson's disease and inherited myoclonus (McCance, K. L. and Huether, S. E. (1994) *Pathophysiology*, Mosby-Year Book, Inc., St. Louis, MO pp. 402–404; Gundlach, A. L. (1990) FASEB J. 4:2761–2766).

3-Hydroxyacyl-CoA dehydrogenase (3HACD) is involved in fatty acid metabolism. It catalyzes the reduction of 3-hydroxyacyl-CoA to 3-oxoacyl-CoA, with concomitant oxidation of NAD to NADH, in the mitochondria and peroxisomes of eukaryotic cells. In peroxisomes, 3HACD and enoyl-CoA hydratase form an enzyme complex called bifunctional enzyme, defects in which are associated with peroxisomal bifunctional enzyme deficiency. This interruption in fatty acid metabolism produces accumulation of very-long chain fatty acids, disrupting development of the brain, bone, and adrenal glands. Infants born with this deficiency typically die within 6 months (Watkins, P. et al. (1989) J. Clin. Invest. 83:771–777; Online Mendelian Inheritance in Man (OMIM), #261515). The neurodegeneration that is characteristic of Alzheimer's disease involves development of extracellular plaques in certain brain regions. A major protein component of these plaques is the peptide amyloid-β (Aβ), which is one of several cleavage products of amyloid precursor protein (APP). 3HACD has been shown to bind the Aβ peptide, and is overexpressed in neurons affected in Alzheimer's disease. In addition, an antibody against 3HACD can block the toxic effects of Aβ in a cell culture model of Alzheimer's disease (Yan, S. et al. (1997) Nature 389:689–695; OMIM, #602057).

17β hydroxysteroid dehydrogenase (17βHSD6) plays an important role in the regulation of the male reproductive hormone, dihydrotestosterone (DHTT). 17βHSD6 acts to reduce levels of DHTT by oxidizing a precursor of DHTT, 3α-diol, to androsterone which is readily glucuronidated and removed from tissues. 17βHSD6 is active with both and estrogen and estrogen substrates when expressed in embryonic kidney 293 cells. At least five other isozymes of 17βHSD have been identified that catalyze oxidation and/or reduction reactions in various tissues with preferences for different steroid substrates (Biswas, M. G. and Russell, D. W. (1997) J. Biol. Chem. 272:15959–15966). For example, 17βHSD1 preferentially reduces estradiol and is abundant in the ovary and placenta. 17βHSD2 catalyzes oxidation of androgens and is present in the endometrium and placenta. 17βHSD3 is exclusively a reductive enzyme in the testis (Geissler, W. M. et al. (1994) Nature Genet. 7:34–39). An excess of androgens such as DHTT can contribute to certain disease states such as benign prostatic hyperplasia and prostate cancer.

Steroids, such as estrogen, testosterone, corticosterone, and others, are generated from a common precursor, cholesterol, and are interconverted into one another. A wide variety of enzymes act upon cholesterol, including a number of dehydrogenases. One such dehydrogenase is 3-oxo-5-α-steroid dehydrogenase (OASD), a microsomal membrane protein highly expressed in prostate and other androgen-responsive tissues. OASD catalyzes the conversion of testosterone into dihydrotestosterone, which is the most potent androgen. Dihydrotestosterone is essential for the formation of the male phenotype during embryogenesis, as well as for proper androgen-mediated growth of tissues such as the prostate and male genitalia. A defect in OASD that prevents the conversion of testosterone into dihydrotestosterone leads to a rare form of male pseudohermaphroditis, characterized by defective formation of the external genitalia (Andersson, S., et al. (1991) Nature 354:159–161; Labrie, F., et al. (1992) Endocrinology 131:1571–1573; OMIM #264600). Thus, OASD plays a central role in sexual differentiation and androgen physiology.

The discovery of new oxidoreductase molecules and the polynucleotides encoding them satisfies a need in the art by providing new compositions which are useful in the diagnosis, prevention, and treatment of cell proliferative disorders including cancer, endocrine, metabolic, reproductive, neurological, autoimmune/inflammatory, and viral disorders.

SUMMARY OF THE INVENTION

The invention features substantially purified polypeptides, oxidoreductase molecules, referred to collectively as "OXRE" and individually as "OXRE-1," "OXRE-2," "OXRE-3," "OXRE-4," "OXRE-5," "OXRE-6," "OXRE-7," "OXRE-8," "OXRE-9," "OXRE-10," "OXRE-11," "OXRE-12," "OXRE-13," "OXRE-14," and "OXRE-15." In one aspect, the invention provides a substantially purified polypeptide comprising an amino acid sequence selected from the group consisting of SEQ ID NO:1–15 and fragments thereof.

The invention further provides a substantially purified variant having at least 90% amino acid identity to at least one of the amino acid sequences selected from the group consisting of SEQ ID NO:1–15 and fragments thereof. The invention also provides an isolated and purified polynucleotide encoding the polypeptide comprising an amino acid sequence selected from the group consisting of SEQ ID NO:1–15 and fragments thereof. The invention also includes an isolated and purified polynucleotide variant having at least 70% polynucleotide sequence identity to the polynucleotide encoding the polypeptide comprising an amino acid sequence selected from the group consisting of SEQ ID NO:1–15 and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1–15 and fragments thereof. The invention also provides an isolated and purified polynucleotide having a sequence which is complementary to the polynucleotide encoding the polypeptide comprising the amino acid sequence selected from the group consisting of SEQ ID NO:1–15 and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention also provides an isolated and purified polynucleotide comprising a polynucleotide sequence selected from the group consisting of SEQ ID NO:16–30 and fragments thereof. The invention further provides an isolated and purified polynucleotide variant having at least 70% polynucleotide sequence identity to the polynucleotide sequence selected from the group consisting of SEQ ID NO:16–30 and fragments thereof. The invention also provides an isolated and purified polynucleotide having a sequence which is complementary to the polynucleotide comprising a polynucleotide sequence selected from the group consisting of SEQ ID NO:16–30 and fragments thereof.

The invention further provides an expression vector containing at least a fragment of the polynucleotide encoding the polypeptide comprising an amino acid sequence selected from the group consisting of SEQ ID NO:1–15 and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1–15 and fragments thereof, in conjunction with a suitable pharmaceutical carrier.

The invention further includes a purified antibody which binds to a polypeptide selected from the group consisting of SEQ ID NO:1–15 and fragments thereof. The invention also provides a purified agonist and a purified antagonist to the polypeptide.

The invention also provides a method for treating or preventing a disorder associated with decreased expression or activity of OXRE, the method comprising administering to a subject in need of such treatment an effective amount of a pharmaceutical composition comprising a substantially purified polypeptide having the amino acid sequence selected from the group consisting of SEQ ID NO:1–15 and fragments thereof, in conjunction with a suitable pharmaceutical carrier.

The invention also provides a method for treating or preventing a disorder associated with increased expression or activity of OXRE, the method comprising administering to a subject in need of such treatment an effective amount of an antagonist of a polypeptide having an amino acid sequence selected from the group consisting of SEQ ID NO:1–15 and fragments thereof.

BRIEF DESCRIPTION OF THE TABLES

Table 1 shows polypeptide and nucleotide sequence identification numbers (SEQ ID NOs), clone identification numbers (clone IDs), cDNA libraries, and cDNA fragments used to assemble full-length sequences encoding OXRE.

Table 2 shows features of each polypeptide sequence, including potential motifs, homologous sequences, and methods and algorithms used for identification of OXRE.

Table 3 shows the tissue-specific expression patterns of each nucleic acid sequence as determined by northern analysis; diseases, disorders, or conditions associated with these tissues; a useful fragment of each nucleic acid; and the vector into which each cDNA was cloned.

Table 4 describes the tissues used to construct the cDNA libraries from which cDNA clones encoding OXRE were isolated.

Table 5 shows the tools, programs, and algorithms used to analyze OXRE, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"OXRE" refers to the amino acid sequences of substantially purified OXRE obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to OXRE, increases or prolongs the duration of the effect of OXRE. Agonists may include proteins, nucleic acids, carbohydrates, or any other molecules which bind to and modulate the effect of OXRE.

An "allelic variant" is an alternative form of the gene encoding OXRE. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding OXRE include those sequences with deletions, insertions, or substitutions of different nucleotides, resulting in a polynucleotide the same as OXRE or a polypeptide with at least one functional characteristic of OXRE. Included within this definition are polymorphisms which may or may not be readily detectable using a particular oligonucleotide probe of the polynucleotide encoding OXRE, and improper or unexpected hybridization to allelic variants, with a locus other than the normal chromosomal locus for the polynucleotide sequence encoding OXRE. The encoded protein may also be "altered," and may contain deletions, insertions, or substitutions of amino acid residues which produce a silent change and result in a functionally equivalent OXRE. Deliberate amino acid substitutions may be made on the basis of similarity in polarity, charge, solubility, hydrophobicity, hydrophilicity, and/or the amphipathic nature of the residues, as long as the biological or immunological activity of OXRE is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of OXRE which are preferably at least 5 to about 15 amino acids in length, most preferably at least 14 amino acids, and which retain some biological activity or immunological activity of OXRE. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to OXRE, decreases the amount or the duration of the effect of the biological or immunological activity of OXRE. Antagonists may include proteins, nucleic acids, carbohydrates, antibodies, or any other molecules which decrease the effect of OXRE.

The term "antibody" refers to intact molecules as well as to fragments thereof, such as Fab, F(ab')$_2$, and Fv fragments, which are capable of binding the epitopic determinant. Antibodies that bind OXRE polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active" refers to a protein having structural, regulatory, or biochemical functions of a naturally occurring molecule. Likewise, "immunologically active" refers to the capability of the natural, recombinant, or synthetic OXRE, or of any oligopeptide thereof, to induce a specific immune response in appropriate animals or cells and to bind with specific antibodies.

The terms "complementary" and "complementarity" refer to the natural binding of polynucleotides by base pairing. For example, the sequence "5'A-G-T 3'" bonds to the complementary sequence "3'T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding OXRE or fragments of OXRE may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using the XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding OXRE, by northern analysis is indicative of the presence of nucleic acids encoding OXRE in a sample, and thereby correlates with expression of the transcript from the polynucleotide encoding OXRE.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" and "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237–244.) Parameters for each method may be the default parameters provided by MEGALIGN or may be specified by the user. The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" and "array element" in a microarray context, refer to hybridizable polynucleotides arranged on the surface of a substrate.

The term "modulate" refers to a change in the activity of OXRE. For example, modulation may cause an increase or a decrease in protein activity, binding characteristics, or any other biological, functional, or immunological properties of OXRE.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which comprise a region of unique polynucleotide sequence that specifically identifies SEQ ID NO:16–30, for example, as distinct from any other sequence in the same genome. For example, a fragment of SEQ ID NO:16–30 is useful in hybridization and amplification technologies and in analogous methods that distinguish SEQ ID NO:16–30 from related polynucleotide sequences. A fragment of SEQ ID NO:16–30 is at least about 15–20 nucleotides in length. The precise length of the fragment of SEQ ID NO:16–30 and the region of SEQ ID NO:16–30 to which the fragment corresponds are routinely determinable by one of ordinary skill in the art based on the intended purpose for the fragment. In some cases, a fragment, when translated, would produce polypeptides retaining some functional characteristic, e.g., antigenicity, or structural domain characteristic, e.g., ATP-binding site, of the full-length polypeptide.

The terms "operably associated" and "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding OXRE, or fragments thereof, or OXRE itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of OXRE polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to OXPE. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human oxidoreductase molecules (OXRE), the polynucleotides encoding OXRE, and the use of these compositions for the diagnosis, treatment, or prevention of cell proliferative disorders including cancer, endocrine, metabolic, reproductive, neurological, autoimmune/inflammatory, and viral disorders.

Table 1 lists the Incyte clones used to assemble full length nucleotide sequences encoding OXRE. Columns 1 and 2 show the sequence identification numbers (SEQ ID NOs) of the polypeptide and nucleotide sequences, respectively. Column 3 shows the clone IDs of the Incyte clones in which nucleic acids encoding each OXRE were identified, and column 4 shows the cDNA libraries from which these clones were isolated. Column 5 shows Incyte clones and their corresponding cDNA libraries. Clones for which cDNA libraries are not indicated were derived from pooled cDNA libraries. The clones in column 5 were used to assemble the consensus nucleotide sequence of each OXRE and are useful as fragments in hybridization technologies.

The columns of Table 2 show various properties of each of the polypeptides of the invention: column 1 references the SEQ ID NO; column 2 shows the number of amino acid residues in each polypeptide; column 3 shows potential phosphorylation sites; column 4 shows potential glycosylation sites; column 5 shows the amino acid residues comprising signature sequences and motifs; column 6 shows the identity of each polypeptide; and column 7 shows analytical methods used to identify each polypeptide through sequence homology and protein motifs.

The columns of Table 3 show the tissue-specificity and diseases, disorders, or conditions associated with nucleotide sequences encoding OXRE. The first column of Table 3 lists the nucleotide SEQ ID NOs. Column 2 lists a fragment of each nucleotide that is useful as described below. Column 3 lists tissue categories which express OXRE as a fraction of total tissues expressing OXRE. Column 4 lists diseases, disorders, or conditions associated with those tissues expressing OXRE as a fraction of total tissues expressing OXRE. Column 5 lists the vectors used to subclone each cDNA library.

The columns of Table 4 show descriptions of the tissues used to construct the cDNA libraries from which cDNA clones encoding OXRE were isolated. Column 1 references the nucleotide SEQ ID NOs, column 2 shows the cDNA libraries from which these clones were isolated, and column 3 shows the tissue origins and other descriptive information relevant to the cDNA libraries in column 2.

Fragments of the nucleotide sequences encoding OXRE, listed in Table 3, Column 2, are useful, for example, in hybridization or amplification technologies to identify SEQ ID NO:16–30 and to distinguish between SEQ ID NO:16–30 and related polynucleotide sequences. The polypeptides encoded by these fragments are useful, for example, as immunogenic peptides.

The invention also encompasses OXRE variants. A preferred OXRE variant is one which has at least about 80%, more preferably at least about 90%, and most preferably at least about 95% amino acid sequence identity to the OXRE amino acid sequence, and which contains at least one functional or structural characteristic of OXRE.

The invention also encompasses polynucleotides which encode OXRE. In a particular embodiment, the invention encompasses a polynucleotide sequence comprising a sequence selected from the group consisting of SEQ ID NO:16–30, which encodes OXRE.

The invention also encompasses a variant of a polynucleotide sequence encoding OXRE. In particular, such a variant polynucleotide sequence will have at least about 70%, more preferably at least about 85%, and most preferably at least about 95% polynucleotide sequence identity to the polynucleotide sequence encoding OXRE. A particular aspect of the invention encompasses a variant of a polynucleotide sequence comprising a sequence selected from the group consisting of SEQ ID NO:16–30 which has at least about 70%, more preferably at least about 85%, and most preferably at least about 95% polynucleotide sequence identity to a nucleic acid sequence selected from the group consisting of SEQ ID NO:16–30. Any one of the polynucleotide variants described above can encode an amino acid sequence which contains at least one functional or structural characteristic of OXRE.

It will be appreciated by those skilled in the art that as a result of the degeneracy of the genetic code, a multitude of polynucleotide sequences encoding OXRE, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring OXRE, and all such variations are to be considered as being specifically disclosed.

Although nucleotide sequences which encode OXRE and its variants are preferably capable of hybridizing to the nucleotide sequence of the naturally occurring OXRE under appropriately selected conditions of stringency, it may be advantageous to produce nucleotide sequences encoding OXRE or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding OXRE and its derivatives without altering the encoded amino acid sequences include the production of RNA transcripts having more desirable properties, such as a greater half-life, than transcripts produced from the naturally occurring sequence.

The invention also encompasses production of DNA sequences which encode OXRE and OXRE derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding OXRE or any fragment thereof.

Also encompassed by the invention are polynucleotide sequences that are capable of hybridizing to the claimed polynucleotide sequences, and, in particular, to those shown in SEQ ID NO:16–30 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier thermal cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding OXRE may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode OXRE may be cloned in recombinant DNA molecules that direct expression of OXRE, or fragments or functional equivalents thereof, in appropriate host cells. Due to the inherent degeneracy of the genetic code, other DNA sequences which encode substantially the same or a functionally equivalent amino acid sequence may be produced and used to express OXRE.

The nucleotide sequences of the present invention can be engineered using methods generally known in the art in order to alter OXRE-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding OXRE may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, OXRE itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin-Elmer). Additionally, the amino acid sequence of OXRE, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman, New York N.Y.)

In order to express a biologically active OXRE, the nucleotide sequences encoding OXRE or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding OXRE. Such elements may vary in their strength and specificity. Specific initiation signals may also be used to achieve more efficient translation of sequences encoding OXRE. Such signals include the ATG initiation codon and adjacent sequences, e.g. the Kozak sequence. In cases where sequences encoding OXRE and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding OXRE and appropriate transcriptional and translational control elements. These methods include in vitro recombinant DNA techniques, synthetic techniques, and in vivo genetic recombination. (See, e.g., Sambrook, J. et al. ( 1989) *Molecular Cloning, A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding OXRE. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus,TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding OXRE. For example, routine cloning, subcloning, and propagation of polynucleotide sequences encoding OXRE can be achieved using a multifunctional *E. coli* vector such as PBLUESCRIPT (Stratagene, La Jolla Calif.) or pSPORT1 plasmid (Life Technologies). Ligation of sequences encoding OXRE into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of OXRE are needed, e.g. for the production of antibodies, vectors which direct high level expression of OXRE may be used. For example, vectors containing the strong, inducible T5 or T7 bacteriophage promoter may be used.

Yeast expression systems may be used for production of OXRE. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of OXRE. Transcription of sequences encoding OXRE may be driven viral promoters, e.g., the 35S and 19S promoters of CAMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding OXRE may be ligated into an adenovirus transcription/translation complex consisting of the late promoter and tripartite leader sequence. Insertion in a non-essential E1 or E3 region of the viral genome may be used to obtain infective virus which expresses OXRE in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of OXRE in cell lines is preferred. For example, sequences encoding OXRE can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; Lowy, I. et al. (1980) Cell 22:817–823.) Also, antimetabolite, antibiotic or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, Calif. (1995) Methods Mol. Biol. 55:121–131.)

Although the presence/absence of marker gene expression suggests that the gene of interest is also present, the presence and expression of the gene may need to be confirmed. For example, if the sequence encoding OXRE is inserted within a marker gene sequence, transformed cells containing sequences encoding OXRE can be identified by the absence of marker gene function. Alternatively, a marker gene can be placed in tandem with a sequence encoding OXRE under the control of a single promoter. Expression of the marker gene in response to induction or selection usually indicates expression of the tandem gene as well.

In general, host cells that contain the nucleic acid sequence encoding OXRE and that express OXRE may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of OXRE using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on OXRE is preferred, but a competitive binding assay may be employed. These and other assays are well known in the art. (See, e.g., Hampton, R. et al. (1990) Serological Methods, a Laboratory Manual, APS Press, St Paul Minn., Sect. IV; Coligan, J. E. et al. (1997) Current Protocols in Immunology, Greene Pub. Associates and Wiley-Interscience, New York N.Y.; and Pound, J. D. (1998) Immunochemical Protocols, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding OXRE include oligolabeling, nick translation, end-labeling, or PCR amplification using a labeled nucleotide. Alternatively, the sequences encoding OXRE, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding OXRE may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode OXRE may be designed to contain signal sequences which direct secretion of OXRE through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Manassas, Va.) and may be chosen to ensure the correct modification and processing of the foreign protein.

In another embodiment of the invention, natural, modified, or recombinant nucleic acid sequences encoding OXRE may be ligated to a heterologous sequence resulting in translation of a fusion protein in any of the aforementioned host systems. For example, a chimeric OXRE protein containing a heterologous moiety that can be recognized by a commercially available antibody may facilitate the screening of peptide libraries for inhibitors of OXRE activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the OXRE encoding sequence and the heterologous protein sequence, so that OXRE may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled OXRE may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of OXRE may be produced not only by recombinant production, but also by direct peptide synthesis using solid-phase techniques. (See, e.g., Creighton, supra, pp. 55–60.) Protein synthesis may be performed by manual techniques or by automation. Automated synthesis may be achieved, for example, using the ABI 431A peptide synthesizer (Perkin-Elmer). Various fragments of OXRE may be synthesized separately and then combined to produce the full length molecule.

Therapeutics

Chemical and structural similarity, e.g., in the context of sequences and motifs, exists between regions of OXRE and oxidoreductase molecules. In addition, the expression of OXRE is closely associated with cell proliferation, cancer, inflammation and immune response, nervous system tissues, and reproductive tissues. Of particular note is the exclusive expression of SEQ ID NO:30 in proliferating brain tissue. Therefore, OXRE appears to play a role in. cell proliferative disorders including cancer, endocrine, metabolic, reproductive, neurological, autoimmune/inflammatory, and viral disorders. In the treatment of cell proliferative disorders including cancer, endocrine, metabolic, reproductive, neurological, autoimmune/inflammatory, and viral disorders associated with increased OXRE expression or activity, it is desirable to decrease the expression or activity of OXRE. In the treatment of the above conditions associated with decreased OXRE expression or activity, it is desirable to increase the expression or activity of OXRE.

Therefore, in one embodiment, OXRE or a fragment or derivative thereof may be administered to a subject to treat or prevent a disorder associated with decreased expression or activity of OXRE. Examples of such disorders include, but are not limited to, a cell proliferative disorder, such as actinic keratosis, arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia; a cancer, such as adenocareinoma, leukemia, lymphoma, melanoma, myeloma, sarcoma, teratocareinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an endocrine disorder such as disorders of the hypothalamus and pituitary resulting from lesions such as primary brain tumors, adenomas, infaretion associated with pregnancy, hypophysectomy, aneurysms, vascular malformations, thrombosis, infections, immunological disorders, and complications due to head trauma; disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; disorders associated with hyperpituitarism including acromegaly, giantism, and syndrome of inappropriate antidiuretic hormone (ADH) secretion (SIADH) often caused by benign adenoma; disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid careinoma, and Plummer's disease; disorders associated with hyperparathyroidism including Conn disease (chronic hypercalemia); pancreatic disorders such as Type I or Type II diabetes mellitus and associated complications; disorders associated with the adrenals such as hyperplasia, careinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease; disorders associated with gonadal steroid hormones such as: in women, abnormal prolactin production, infertility, endometriosis, perturbations of the menstrual cycle, polycystic ovarian disease, hyperprolactinemia, isolated gonadotropin deficiency, amenorrhea, galactorrhea, hermaphroditism, hirsutism and virilization, breast cancer, and, in post-menopausal women, osteoporosis; and, in men, Leydig cell deficiency, male climacteric phase, and germinal cell aplasia, hypergonadal disorders associated with Leydig cell tumors, androgen resistance associated with absence of androgen receptors, syndrome of 5 α-reductase, and gynecomastia; a metabolic disorder, such as Addison's disease, cystic fibrosis, diabetes, fatty hepatocirrhosis, galactosemia, goiter, hyperadrenalism, hypoadrenalism, hyperparathyroidism, hypoparathyroidism, hypercholesterolemia, hyperthyroidism, hypothyroidism hyperlipidemia, hyperlipemia, lipid myopathies, obesity, lipodystrophies, and phenylketonuria, congenital adrenal hyperplasia, pseudovitamin D-deficiency rickets, cerebrotendinous xanthomatosis, and coumarin resistance; a reproductive disorder such as disorders of prolactin production, infertility, including tubal disease, ovulatory defects, and endometriosis, disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeluetal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; seasonal affective disorder (SAD); akathesia, amnesia, catatonia, diabetic neuropathy, tardive dyskinesia, dystonias, paranoid psychoses, postherpetic neuralgia, and Tourette's disorder; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis. osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and a viral disorder, such as viral infections, e.g., those caused by adenoviruses (acute respiratory disease, pneumonia), arenaviruses (lymphocytic choriomeningitis), bunyaviruses (Hantavirus), coronaviruses (pneumonia, chronic bronchitis), hepadnaviruses (hepatitis), herpesviruses (herpes simplex virus, varicella-zoster virus, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (human immunodeficiency virus, human T lymphotropic virus), rhabdoviruses (rabies), rotaviruses (gastroenteritis), and togaviruses (encephalitis, rubella).

In another embodiment, a vector capable of expressing OXRE or a fragment or derivative thereof may be administered to a subject to treat or prevent a disorder associated with decreased expression or activity of OXRE including, but not limited to, those described above.

In a further embodiment, a pharmaceutical composition comprising a substantially purified OXRE in conjunction with a suitable pharmaceutical carrier may be administered to a subject to treat or prevent a disorder associated with decreased expression or activity of OXRE including, but not limited to, those provided above.

In still another embodiment, an agonist which modulates the activity of OXRE may be administered to a subject to treat or prevent a disorder associated with decreased expression or activity of OXRE including, but not limited to, those listed above.

In a further embodiment, an antagonist of OXRE may be administered to a subject to treat or prevent a disorder associated with increased expression or activity of OXRE. Examples of such disorders include, but are not limited to, those described above. In one aspect, an antibody which specifically binds OXRE may be used directly as an antagonist or indirectly as a targeting or delivery mechanism for bringing a pharmaceutical agent to cells or tissue which express OXRE.

In an additional embodiment, a vector expressing the complement of the polynucleotide encoding OXRE may be administered to a subject to treat or prevent a disorder associated with increased expression or activity of OXRE including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of OXRE may be produced using methods which are generally known in the art. In particular, purified OXRE may be used to produce antibodies or to screen libraries of pharmaceutical agents to identify those which specifically bind OXRE. Antibodies to OXRE may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with OXRE or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to OXRE have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of OXRE amino acids may be fused with those of another protein, such as KLH, and antibodies to the chimeric molecule may be produced.

Monoclonal antibodies to OXRE may be prepared using any technique which provides for the production of antibody molecules by continuous cell lines in culture. These include, but are not limited to, the hybridoma technique, the human B-ell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce OXRE-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for OXRE may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between OXRE and its specific antibody. A two-site, monoclonal-based immunoassay utilizing monoclonal antibodies reactive to two non-interfering OXRE epitopes is preferred, but a competitive binding assay may also be employed (Pound, supra).

Various methods such as Scatchard analysis in conjunction with radioimmunoassay techniques may be used to assess the affinity of antibodies for OXRE. Affinity is expressed as an association constant, $K_a$, which is defined as the molar concentration of OXRE-antibody complex divided by the molar concentrations of free antigen and free antibody under equilibrium conditions. The $K_a$ determined for a preparation of polyclonal antibodies, which are heterogeneous in their affinities for multiple OXRE epitopes, represents the average affinity, or avidity, of the antibodies for OXRE. The $K_a$ determined for a preparation of monoclonal antibodies, which are monospecific for a particular OXRE epitope, represents a true measure of affinity. High-affinity antibody preparations with $K_a$ ranging from about $10^9$ to $10^{12}$ L/mole are preferred for use in immunoassays in which the OXRE-antibody complex must withstand rigorous manipulations. Low-affinity antibody preparations with $K_a$ ranging from about $10^6$ to $10^7$ L/mole are preferred for use in immunopurification and similar procedures which ultimately require dissociation of OXRE, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of OXRE-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding OXRE, or any fragment or complement thereof, may be used for therapeutic purposes. In one aspect, the complement of the polynucleotide encoding OXRE may be used in situations in which it would be desirable to block the transcription of the mRNA. In particular, cells may be transformed with sequences complementary to polynucleotides encoding OXRE. Thus, complementary molecules or fragments may be used to modulate OXRE activity, or to achieve regulation of gene function. Such technology is now well known in the art, and sense or antisense oligonucleotides or larger fragments can be designed from various locations along the coding or control regions of sequences encoding OXRE.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding OXRE. (See, e.g., Sambrook, supra; Ausubel, 1995, supra.)

Genes encoding OXRE can be turned off by transforming a cell or tissue with expression vectors which express high levels of a polynucleotide, or fragment thereof, encoding OXRE. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding OXRE. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding OXRE.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding OXRE. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of OXRE, antibodies to OXRE, and mimetics, agonists, antagonists, or inhibitors of OXRE. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of OXRE, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example OXRE or fragments thereof, antibodies of OXRE, and agonists, antagonists or inhibitors of OXRE, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind OXRE may be used for the diagnosis of disorders characterized by expression of OXRE, or in assays to monitor patients being treated with OXRE or agonists, antagonists, or inhibitors of OXRE. Antibodies useful for diagnostic purposes may be prepared in the same manner as described above for therapeutics. Diagnostic assays for OXRE include methods which utilize the antibody and a label to detect OXRE in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring OXRE, including ELISAs, RIAs, and FACS, are known in the art and provide a basis for diagnosing altered or abnormal levels of OXRE expression. Normal or standard values for OXRE expression are established by combining body fluids or cell extracts taken from normal mammalian subjects, preferably human, with antibody to OXRE under conditions suitable for complex formation. The amount of standard complex formation may be quantitated by various methods, preferably by photometric means. Quantities of OXRE expressed in subject, control, and disease samples from biopsied tissues are compared with the standard values. Deviation between standard and subject values establishes the parameters for diagnosing disease.

In another embodiment of the invention, the polynucleotides encoding OXRE may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of OXRE may be correlated with disease. The diagnostic assay may be used to determine absence, presence, and excess expression of OXRE, and to monitor regulation of OXRE levels during therapeutic intervention.

In one aspect, hybridization with PCR probes which are capable of detecting polynucleotide sequences, including genomic sequences, encoding OXRE or closely related molecules may be used to identify nucleic acid sequences which encode OXRE. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding OXRE, allelic variants, or related sequences.

Probes may also be used for the detection of related sequences, and should preferably have at least 50% sequence identity to any of the OXRE encoding sequences. The hybridization probes of the subject invention may be DNA or RNA and may be derived from the sequence of SEQ ID NO:16–30 or from genomic sequences including promoters, enhancers, and introns of the OXRE gene.

Means for producing specific hybridization probes for DNAs encoding OXRE include the cloning of polynucleotide sequences encoding OXRE or OXRE derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $_{35}S$, or by enzymatic labels, such as alkaline phosphatase coupled to the probe via avidin/biotin coupling systems, and the like.

Polynucleotide sequences encoding OXRE may be used for the diagnosis of disorders associated with expression of OXRE. Examples of such disorders include, but are not limited to, a cell proliferative disorder, such as such as actinic keratosis, arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia; a cancer, such as adenocareinoma, leukemia, lymphoma, melanoma, myeloma, sarcoma, teratocareinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an endocrine disorder such as disorders of the hypothalamus and pituitary resulting from lesions such as primary brain tumors, adenomas, infaretion associated with pregnancy, hypophysectomy, aneurysms, vascular malformations, thrombosis, infections, immunological disorders, and complications due to head trauma; disorders associated with hypopituitarism including hypogonadism, Sheehan syndrome, diabetes insipidus, Kallman's disease, Hand-Schuller-Christian disease, Lettrer-Siwe disease, sareoidosis, empty sella syndrome, and dwarfism; disorders associated with hyperpituitarism including acromegaly, giantism, and syndrome of inappropriate antidiuretic hormone (ADH) secretion (SIADH) often caused by benign adenoma; disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid careinoma, and Plummer's disease; disorders associated with hyperparathyroidism including Conn disease (chronic hypercalemia); pancreatic disorders such as Type I or Type II diabetes mellitus and associated complications; disorders associated with the adrenals such as hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease; disorders associated with gonadal steroid hormones such as: in women, abnormal prolactin production, infertility, endometriosis, perturbations of the menstrual cycle, polycystic ovarian disease, hyperprolactinemia, isolated gonadotropin deficiency, amenorrhea, galactorrhea, hermaphroditism, hirsutism and virilization, breast cancer, and, in post-menopausal women, osteoporosis; and, in men, Leydig cell deficiency, male climacteric phase, and germinal cell aplasia, hypergonadal disorders associated with Leydig cell tumors, androgen resistance associated with absence of androgen receptors, syndrome of 5 α-reductase, and gynecomastia; a metabolic disorder, such as Addison's disease, cystic fibrosis, diabetes, fatty hepatocirrhosis, galactosemia, goiter, hyperadrenalism, hypoadrenalism, hyperparathyroidism, hypoparathyroidism, hypercholesterolemia, hyperthyroidism, hypothyroidism hyperlipidemia, hyperlipemia, lipid myopathies, obesity, lipodystrophics, and phenylketonuria, congenital adrenal hyperplasia, pseudovitamin D-deficiency rickets, cerebrotendinous xanthomatosis, and coumarin resistance; a reproductive disorder such as disorders of prolactin production, infertility, including tubal disease, ovulatory defects, and endometriosis, disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; seasonal affective disorder (SAD); akathesia, amnesia, catatonia, diabetic neuropathy, tardive dyskinesia, dystonias, paranoid psychoses, postherpetic neuralgia, and Tourette's disorder;

an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scieroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and a viral disorder, such as viral infections, e.g., those caused by adenoviruses (acute respiratory disease, pneumonia), arenaviruses (lymphocytic choriomeningitis), bunyaviruses (Hantavirus), coronaviruses (pneumonia, chronic bronchitis), hepadnaviruses (hepatitis), herpesviruses (herpes simplex virus, varicella-zoster virus, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (human immunodeficiency virus, human T lymphotropic virus), rhabdoviruses (rabies), rotaviruses (gastroenteritis), and togaviruses (encephalitis, rubella). The polynucleotide sequences encoding OXRE may be used in Southern or northern analysis, dot blot, or other membrane-based technologies; in PCR technologies; in dipstick, pin, and multi-format ELISA-like assays; and in microarrays utilizing fluids or tissues from patients to detect altered OXRE expression. Such qualitative or quantitative methods are well known in the art.

In a particular aspect, the nucleotide sequences encoding OXRE may be useful in assays that detect the presence of associated disorders, particularly those mentioned above. The nucleotide sequences encoding OXRE may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding OXRE in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of OXRE, a normal or standard profile for expression is established. This may be accomplished by combining body fluids or cell extracts taken from normal subjects, either animal or human, with a sequence, or a fragment thereof, encoding OXRE, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding OXRE may involve the use of PCR. These oligomers may be chemically synthesized, generated enzymatically, or produced in vitro. Oligomers will preferably contain a fragment of a polynucleotide encoding OXRE, or a fragment of a polynucleotide complementary to the polynucleotide encoding OXRE, and will be employed under optimized conditions for identification of a specific gene or condition. Oligomers may also be employed under less stringent conditions for detection or quantitation of closely related DNA or RNA sequences.

Methods which may also be used to quantify the expression of OXRE include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding OXRE may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding OXRE on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, OXRE, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between OXRE and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with OXRE, or fragments thereof, and washed. Bound OXRE is then detected by methods well known in the art. Purified OXRE can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding OXRE specifically compete with a test compound for binding OXRE. In this manner, antibodies can be used to detect the presence of any peptide which shares one or more antigenic determinants with OXRE.

In additional embodiments, the nucleotide sequences which encode OXRE may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all patents, applications, and publications mentioned above and below, in particular U.S. Ser. No. 60/172,227, filed Oct. 6, 1998, U.S. Ser. No. 60/155,202, filed Dec. 2, 1998, and U.S. Ser. No. 60/123,911, are hereby expressly incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), pSPORT1 plasmid (Life Technologies), or pINCY (Incyte Pharmaceuticals, Palo Alto Calif.). Recombinant plasmids were transformed into competent E. coli cells including XL1-Blue, XL1-BlueMRF, or SOLR from Stratagene or DH5α, DH10B, or ElectroMAX DH10B from Life Technologies.

II. Isolation of cDNA Clones

Plasmids were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a Fluoroskan II fluorescence scanner (Labsystems Oy, Helsinki, Finland).

III. Sequencing and Analysis cDNA sequencing reactions were processed using standard methods or high-throughput instrumentation such as the ABI CATALYST 800 (Perkin-Elmer) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Perkin-Elmer). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Perkin-Elmer) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example V.

The polynucleotide sequences derived from cDNA sequencing were assembled and analyzed using a combination of software programs which utilize algorithms well known to those skilled in the art. Table 5 summarizes the tools, programs, and algorithms used and provides applicable descriptions, references, and threshold parameters. The first column of Table 5 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score, the greater the homology between two sequences). Sequences were analyzed using MACDNASIS PRO software (Hitachi Software Engineering, South San Francisco Calif.) and LASERGENE software (DNASTAR). Polynucleotide and polypeptide sequence alignments were generated using the default parameters specified by the clustal algorithm as incorporated into the MEGALIGN multisequence alignment program (DNASTAR), which also calculates the percent identity between aligned sequences.

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as the GenBank primate, rodent, mammalian, vertebrate, and eukaryote databases, and BLOCKS to acquire annotation using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probabilistic approach which analyzes consensus primary structures of gene families. (See, e.g., Eddy, S. R. (1996) Curr. Opin. Str. Biol. 6:361–365.)

The programs described above for the assembly and analysis of full length polynucleotide and amino acid sequences were also used to identify polynucleotide sequence fragments from SEQ ID NO:16–30. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding OXRE occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Extension of OXRE Encoding Polynucleotides

The full length nucleic acid sequences of SEQ ID NO:16–30 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2×carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequences of SEQ ID NO:16–30 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:16–30 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250μCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. Hybridization patterns are visualized using autoradiography and compared.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the OXRE-encoding sequences, or any parts thereof, are used to detect, decrease, or inhibit expression of naturally occurring OXRE. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of OXRE. To inhibit transcription, a complementary oligonucleotide is designed from the most unique 5' sequence and used to prevent promoter binding to the coding sequence. To inhibit translation, a complementary oligonucleotide is designed to prevent ribosomal binding to the OXRE-encoding transcript.

IX. Expression of OXRE

Expression and purification of OXRE is achieved using bacterial or virus-based expression systems. For expression of OXRE in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express OXRE upon induction with isopropyl beta-D-thiogalactopyranoside (IPTG). Expression of OXRE in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding OXRE by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, OXRE is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from OXRE at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified OXRE obtained by these methods can be used directly in the following activity assay.

X. Demonstration of OXRE Activity

For purposes of example, an assay demonstrating the activity of a short-chain alcohol dehydrogenase is described. Essentially the same method is used for other types of oxidoreductases, with suitable substitution of the substrate and electron acceptor. OXRE activity is demonstrated by the oxidation of NADPH to NADP in the presence of substrate (Kunau and Dommes (1978) Eur. J. Biochem. 91:533–544). Substrates include, but are not limited to, all-trans-retinaldehyde and cis-4-dienoyl-CoA. OXRE is preincubated for 10 minutes at 37° C. in 60 µM potassium phosphate (pH 7.4), 125 nM NADPH, and 0.2 µM CoA (coenzyme A). The reaction is initiated by addition of the appropriate substrate (12.5 to 150 µM final concentration). The change in absorbance of the reaction at 340 nm, due to the oxidation of NADPH to NADP, is measured using a spectrophotometer at 23° C. Units of OXRE activity are expressed as pmoles of NADP formed per minute. A reaction lacking OXRE is used as a negative control.

Alternatively, OXRE activity is assayed by measuring the reduction of insulin. Aliquots of OXRE are preincubated at 37° C. for 20 min with 2 µl of 50 mM Hepes, pH 7.6, 100 µg/ml bovine serum albumin, and 2 mM DTT in a total volume of 70 µl. Then, 40 µl of a reaction mixture composed of 200 µl of Hepes (1 M), pH 7.6, 40 µl of EDTA (0.2 M), 40 µl of NADPH (40 mg/ml), and 500 µl of insulin (10 mg/ml) is added. The reaction is initiated with the addition of 10 µl of thioredoxin reductase from calf thymus (3.0 A412 unit), and incubation is continued for 20 min at 37° C. The reaction rate is followed by monitoring the oxidation of NADPH at 412 nM. The oxidation of NADPH is proportional to the amount of insulin reduction.

XI. Functional Assays

OXRE function is assessed by expressing the sequences encoding OXRE at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of OXRE on gene expression can be assessed using highly purified populations of cells transfected with sequences encoding OXRE and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding OXRE and other genes of interest can be analyzed by northern analysis or microarray techniques.

XII. Production of OXRE Specific Antibodies

OXRE substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the OXRE amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 4311A peptide synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit 1 gG.

XIII. Purification of Naturally Occurring OXRE Using Specific Antibodies

Naturally occurring or recombinant OXRE is substantially purified by immunoaffinity chromatography using antibodies specific for OXRE. An immunoaffinity column is constructed by covalently coupling anti-OXRE antibody to an activated chromatographic resin, such as CNBr-activated SEPHAROSE (Amersham Pharmacia Biotech). After the coupling, the resin is blocked and washed according to the manufacturer's instructions.

Media containing OXRE are passed over the immunoaffinity column, and the column is washed under conditions that allow the preferential absorbance of OXRE (e.g., high ionic strength buffers in the presence of detergent). The column is eluted under conditions that disrupt antibody/OXRE binding (e.g., a buffer of pH 2 to pH 3, or a high concentration of a chaotrope, such as urea or thiocyanate ion), and OXRE is collected.

XIV. Identification of Molecules Which Interact with OXRE

OXRE, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled OXRE, washed, and any wells with labeled OXRE complex are assayed. Data obtained using different concentrations of OXRE are used to calculate values for the number, affinity, and association of OXRE with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Protein SEQ ID NO: | Nucleotide SEQ ID NO: | Clone ID | Library | Fragments |
|---|---|---|---|---|
| 1 | 16 | 000746 | U937NOT01 | 000746H, 000746X777, and 002067R1 (U937NOT01), 1304321T1 (PLACNOT02), 967947R1 (BRSTNOT05), SAPA01383F1, SXAA00973D1 |
| 2 | 17 | 2472577 | THP1NOT03 | 755151R1 (BRAITUT02), 2472577H1 (THP1NOT03), 2476593F6 (SMCANOT01) |
| 3 | 18 | 2160405 | ENDCNOT02 | 1579324T6 (DUODNOT01), 1929782F6 (COLNTUT03), 1984568R6 (LUNGAST01), 1984568T6 (LUNGAST01), 2160405H1 (ENDCNOT02), 3088049F6 (HEAONOT03), SBMA01335F1 |
| 4 | 19 | 2591695 | LUNGNOT22 | 1293773H1 (PGANNOT03), 1981831H1 (LUNGTUT03), 2591695H1 (LUNGNOT22), 2599633T6 (UTRSNOT10), 3079232H1 (BRAIUNT01), 3388467H1 (LUNGTUT17), 3728027F6 (SMCCNON03) |
| 5 | 20 | 474100 | MMLR1DT01 | 474100H1 (MMLR1DT01), 831142H1 and 1543031T1 (PROSTUT04), 1579546F6 (DUODNOT01), 1833969T6 (BRAINON01), 2360323H1 (LUNGFET05), 2571957H1 (HIPOAZT01), 3584211F6 (293TF4T01), SAIA02772F1 |
| 6 | 21 | 1304767 | PLACNOT02 | 737411X28R1 (TONSNOT01), 1304767H1 (PLACNOT02), 1429123T1 (SINTBST01), 1458173R1 (COLNFET02), 1594353T6 (BRAINOT14) |
| 7 | 22 | 1465978 | PANCTUT02 | 872915R1 (LUNGAST01), 1465978F6 and 1465978H1 (PANCTUT02), 1865790F6 (PROSNOT19), 2062093R6 and 2132634T6 (OVARNOT03), 2232155F6 (PROSNOT16), 2521685H1 (BRAITUT21), 3037185H1 (SMCCNOT02) |

TABLE 1-continued

| Protein SEQ ID NO: | Nucleotide SEQ ID NO: | Clone ID | Library | Fragments |
|---|---|---|---|---|
| 8 | 23 | 1635966 | UTRSNOT06 | 108553F1 (AMLBNOT01), 816384R1 (OVARTUT01), 1635966H1 (UTRSNOT06), 3076973H1 (BONEUNT01), SBBA03935F1, SBBA00704F1, SBBA05518F1 |
| 9 | 24 | 1638410 | UTRSNOT06 | 986854R1 (LVENNOT03), 1297217T1 (BRSTNOT07), 1442549F1 (THYRNOT03), 1542919R1 (PROSTUT04), 1621602F6 (BRAITUT13), 1638410H1 (UTRSNOT06), 1867420F6 (SKINBIT01), 3721081H1 (PENCNOT10), 3770890H1 (BRSTNOT25) |
| 10 | 25 | 1743409 | HIPONON01 | 190557F1 and 190557R1 (SYNORAB01), 1743409H1 and 1743409R6 (HIPONON01), 3725583H1 (BRSTNOT23) |
| 11 | 26 | 1803830 | SINTNOT13 | 1611528T6 (COLNTUT06), 1803830H1, 1803830T6, 1803830X12F1 and 1803830X15F1 (SINTNOT13) |
| 12 | 27 | 1867333 | SKINBIT01 | 068790F1 and 068790R1 (HUVESTB01), 1209587R1 (BRSTNOT02), 1498674F6 (SINTBST01), 1519693F6 and 1520517F1 (BLADTUT04), 1867333H1 (SKINBIT01), 1958915H1 (CONNNOT01), 2537783H1 (BONRTUT01), 2638196F6 (BONTNOT01), 3039056H1 (BRSTNOT16), 4051183H1 (SINTNOT18), 4228470H1 (BRAMDIT01) |
| 13 | 28 | 2906094 | THYMNOT05 | 1442945F6 (THYRNOT03), 1711329X17C1 and 1711654X21C1 (PROSNOT16), 2309777H1 (NGANNOT01), 2906094H1 (THYMNOT05) |
| 14 | 29 | 3294314 | TLYJINT01 | 1528021F1 (UCMCL5T01), 2207228T6 (SINTFET03), 3294314H1 (TLYJINT01), 3333445F6 (BRAIFET01) |
| 15 | 30 | 4940951 | BRAIFEN03 | 4940951F6, 4940951H1, and 4940951T6 (BRAIFEN03) |

TABLE 2

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 1 | 280 | S68 T119 S128 S247 T257 S92 S209 S221 T257 T277 | | Thioredoxin domain: R28-E131 Thioredoxin family active site: P36-V78 | Thioredoxin | Motifs PFAM PROFILESCAN |
| 2 | 166 | S26 S56 S136 S150 T158 | | Q2-C162 | C1-tetrahydrofolate dehydrogenase (GI901850) | Motifs BLAST BLOCKS PRINTS PFAM |
| 3 | 319 | S61 S67 S111 T167 S216 S218 S250 | | V9-D283 | Lambda crystallin (GI164905) | Motifs BLAST PFAM BLOCKS |
| 4 | 318 | S140 T191 Y149 | | | 3-Oxo-5-alpha-steroid dehydrogenase (GI401056) | Motifs BLAST |
| 5 | 330 | T158 S247 T253 S294 S203 S239 | N204 | Transmembrane region: F117-F136 | dTDP-6-deoxy-L-mannose dehydrogenase GI 1314582 | BLAST, HMM, MOTIFS, PRINTS |
| 6 | 266 | T60 T201 T235 T257 T72 | N134 | Short-chain dehydrogenase: K10-P186 G212-V241 | Glucose dehydrogenase GI 216268 | BLAST, PFAM, HMM, MOTIFS, BLOCKS, PRINTS |
| 7 | 302 | T79 S131 S135 T222 T72 T106 T154 T190 T297 | | Short-chain dehydrogenase: E39-T216 | Retinal short-chain dehydrogenase GI 3450828 | BLAST, PFAM, HMM, MOTIFS, BLOCKS, PRINTS |
| 8 | 300 | S33 S286 T52 S95 T198 T267 S103 T151 S187 | | Short-chain dehydrogenase: E37-G224 Signal Peptide: M1-S18 | Retinal short-chain dehydrogenase GI 3450830 | BLAST, PFAM HMM, MOTIFS, BLOCKS, PRINTS |
| 9 | 613 | T87 S116 S118 S213 S268 T512 S519 S530 S532 T534 S27 T87 S149 T190 T229 T263 S376 S461 Y95 | N186 N350 N468 | Pyridine nucleotide-disulphide oxidoreductase: F134-Q523 | Putative ferredoxin reductase MOCF GI 3411185 | BLAST, PFAM, HMM, MOTIFS, BLOCKS, PRINTS |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 10 | 325 | T150 T154 S268 T6 T106 S146 Y167 | N243 | Short-chain dehydrogenase: A53-N243, S194-R222 Transmembrane region: F18-L37 | Similar to the insect-type alcohol dehydrogenase GI 1125838 | BLAST, PFAM, HMM, MOTIFS, BLOCKS, PRINTS |
| 11 | 421 | T119 T126 S169 S228 T406 T108 T202 T413 Y247 | | | Gamma-Butyrobetaine hydroxylase GI 3746805 | BLAST, MOTIFS |
| 12 | 610 | S484 T46 S151 S241 T397 T414 S444 T449 T466 S492 T564 S335 T380 T488 S551 | N271 | Pyridine nucleotide-disulphide oxidoreductase: V70-E341 Signal Peptide: M1-C18 | Pyridine nucleotide-disulphide oxidoreductase | HMM, PFAM, MOTIFS |
| 13 | 415 | S33 S101 S165 T318 S175 | N186 | Acyl CoA dehydrogenase: L41-R410 | Acyl CoA reductase (fadE9) GI 2911026 | BLAST, PFAM, HMM, MOTIFS, BLOCKS |
| 14 | 274 | S61 S108 T109 S259 S7 T44 T216 T265 | | Delta 1-pyrroline-5-carboxylate reductase: R9-A256 | Pyrroline-5-carboxylate reductase GI 189498 | BLAST, PFAM, HMM, MOTIFS, BLOCKS |
| 15 | 283 | S83 S28 S90 S129 S137 S252 T46 S239 S244 | N114 | Aldehyde ferredoxin oxidoreductase: P102-N114 Transmembrane region: F260-I279 | Aldehyde ferredoxin oxidoreductase | HMM, BLOCKS |

TABLE 3

| Nucleotide SEQ ID NO: | Useful Fragment | Tissue Expression (Fraction of Total) | Disease or Condition (Fraction of Total) | Vector |
|---|---|---|---|---|
| 16 | 112–147 | | Cell proliferative (0.68) Inflammation/immune (0.26) | pBLUESCRIPT |
| 17 | 189–218 | Cardiovascular (0.500) Hematopoietic/Immune (0.125) Musculoskeletal (0.125) | Cancer (0.625) Inflammation (0.250) | |
| 18 | 597–626 | Reproductive (0.225) Gastrointestinal (0.197) Hematopoietic/Immune (0.127) | Cancer (0.620) Inflammation (0.254) | |
| 19 | 57–86 | Gastrointestinal (0.217) Cardiovascular (0.174) Reproductive (0.130) | Cancer (0.652) Inflammation (0.217) | |
| 20 | 1028–1072 | Nervous (0.202) Reproductive (0.177) Gastrointestinal (0.129) | Cancer (0.395) Inflammation (0.290) Cell proliferative (0.161) | PSPORT1 |
| 21 | 651–695 | Nervous (0.286) Hematopoietic/Immune (0.143) Reproductive (0.143) | Cancer (0.393) Cell proliferative (0.214) Inflammation (0.214) | pINCY |
| 22 | 619–663 | Reproductive (0.296) Gastrointestinal (0.185) Nervous (0.141) | Cancer (0.526) Cell proliferative (0.185) Inflammation (0.185) | pINCY |
| 23 | 1034–1078 | Reproductive (0.211) Gastrointestinal (0.203) Hematopoietic/Immune (0.148) | Cancer (0.469) Inflammation (0.289) Cell proliferative (0.180) | pINCY |
| 24 | 768–812 | Reproductive (0.306) Cardiovascular (0.139) Nervous (0.139) | Cancer (0.500) Inflammation (0.250) Cell proliferative (0.139) | pINCY |
| 25 | 999–1043 | Reproductive (0.365) Cardiovascular (0.115) Gastrointestinal (0.096) | Cancer (0.500) Inflammation (0.231) Cell proliferative (0.173) | PSPORT1 |
| 26 | 642–686 | Reproductive (0.500) Gastrointestinal (0.125) Developmental (0.083) | Cancer (0.542) Cell proliferative (0.167) Inflammation (0.167) | pINCY |
| 27 | 56–100 | Reproductive (0.301) Gastrointestinal (0.221) Nervous (0.106) | Cancer (0.540) Inflammation (0.248) Cell proliferative (0.097) | pINCY |
| 28 | 1258–1302 | Reproductive (0.333) Nervous (0.194) Hematopoietic/Immune (0.139) | Cancer (0.583) Cell proliferative (0.194) Inflammation (0.194) | pINCY |

TABLE 3-continued

| Nucleotide SEQ ID NO: | Useful Fragment | Tissue Expression (Fraction of Total) | Disease or Condition (Fraction of Total) | Vector |
|---|---|---|---|---|
| 29 | 57–101 | Developmental (0.214) Nervous (0.214) Hematopoietic/Immune (0.143) | Cancer (0.500) Cell proliferative (0.429) Inflammation (0.143) | pINCY |
| 30 | 35–79 | Nervous (1.000) | Cell proliferative (1.000) | pINCY |

TABLE 4

| Polynucleotide SEQ ID NO: | Library | Library Comment |
|---|---|---|
| 16 | U937NOT01 | The U-937 cDNA library, U937NOT01, was constructed at Stratagene using RNA isolated from the U937 monocyte-like cell line. This cell line (ATCC CRL1593) was established by C. Sundstrom and K. Nilsson in 1974 from cells obtained from the pleural effusion of a 37-year-old Caucasian male with diffuse histiocytic lymphoma. |
| 17 | THP1NOT03 | Library was constructed using RNA isolated from untreated THP-1 cells. THP-1 (ATCC TIB 202) is a human promonocyte cell line derived from the peripheral blood of a 1-year-old Caucasian male with acute monocytic leukemia. |
| 18 | ENDCNOT02 | Library was constructed using RNA isolated from dermal microvascular endothelial cells removed from a 30-year-old Caucasian female. |
| 19 | LUNGNOT22 | Library was constructed using RNA isolated from lung tissue removed from a 58-year-old Caucasian female. The tissue sample used to construct this library was found to have tumor contaminant upon microscopic examination. Pathology for the associated tumor tissue indicated a caseating granuloma. Family history included congestive heart failure, breast cancer, secondary bone cancer, acute myocardial infarction and atherosclerotic coronary artery disease. |
| 20 | MMLR1DT01 | Library was constructed using RNA isolated from adherent mononuclear cells, which came from a pool of male and female donors. The cells were cultured for 24 hours following Ficoll Hypaque centrifugation. |
| 21 | PLACNOT02 | Library was constructed using RNA isolated from the placental tissue of a Hispanic female fetus, who was prematurely delivered at 21 weeks' gestation. |
| 22 | PANCTUT02 | Library was constructed using RNA isolated from pancreatic tumor tissue removed from a 45-year-old Caucasian female during radical pancreaticoduodenectomy. Pathology indicated a grade 4 anaplastic carcinoma. Family history included benign hypertension, hyperlipidemia and atherosclerotic coronary artery disease. |
| 23 | UTRSNOT06 | Library was constructed using RNA isolated from myometrial tissue removed from a 50-year-old Caucasian female during a vaginal hysterectomy. Pathology indicated residual atypical complex endometrial hyperplasia. Pathology for the associated tissue removed during dilation and curettage indicated fragments of atypical complex hyperplasia and a single microscopic focus suspicious for grade 1 adenocarcinoma. Patient history included benign breast neoplasm, hypothyroid disease, polypectomy, and arthralgia. Family history included cerebrovascular disease, atherosclerotic coronary artery disease, hyperlipidemia, and chronic hepatitis. |
| 24 | UTRSNOT06 | Library was constructed using RNA isolated from myometrial tissue removed from a 50-year-old Caucasian female during a vaginal hysterectomy. Pathology indicated residual atypical complex endometrial hyperplasia. Pathology for the associated tissue removed during dilation and curettage indicated fragments of atypical complex hyperplasia and a single microscopic focus suspicious for grade 1 adenocarcinoma. Patient history included benign breast neoplasm, hypothyroid disease, polypectomy, and arthralgia. Family history included cerebrovascular disease, atherosclerotic coronary artery disease, hyperlipidemia, and chronic hepatitis. |
| 25 | HIPONON01 | This normalized hippocampus library was constructed from 1.13 million independent clones from a hippocampus library. RNA was isolated from the hippocampus tissue of a 72-year-old Caucasian female who died from an intracranial bleed. Patient history included nose cancer, hypertension, and arthritis. The normalization and hybridization conditions were adapted from Soares et al. (PNAS (1994) 91:9928). |

TABLE 4-continued

| Polynucleotide SEQ ID NO: | Library | Library Comment |
|---|---|---|
| 26 | SINTNOT13 | Library was constructed using RNA isolated from ileum tissue obtained from a 25-year-old Asian female during a partial colectomy and temporary ileostomy. Pathology indicated moderately active chronic ulcerative colitis, involving colonic mucosa from the distal margin to the ascending colon. Family history included hyperlipidemia, depressive disorder, malignant cervical neoplasm, viral hepatitis A, and depressive disorder. |
| 27 | SKINBIT01 | Library was constructed using RNA isolated from diseased skin tissue of the left lower leg. Patient history included erythema nodosum of the left lower leg. |
| 28 | THYMNOT05 | Library was constructed using RNA isolated from thymus tissue removed from a 3-year-old Hispanic male during thymectomy and closure of a patent ductus arteriosus. The patient presented with severe pulmonary stenosis and cyanosis. Patient history included cardiac catheterization, echocardiogram, and corrective cardiac surgeries. |
| 29 | TLYJINT01 | Library was constructed using RNA isolated from a Jurkat cell line derived from the T cells of a male. The cells were treated for 18 hours with 50 ng/ml phorbol ester and 1 $\mu$M calcium ionophore. Patient history included acute T-cell leukemia. |
| 30 | BRAIFEN03 | This normalized fetal brain tissue library was constructed from 3.26 million independent clones from a fetal brain library. Starting RNA was made from brain tissue removed from a Caucasian male fetus with a hypoplastic left heart stillborn after 23 weeks' gestation. The library was normalized in two rounds (with 48 hour reannealing hybridizations) using conditions adapted from Soares et al. (PNAS (1994) 91:9228) and Bonaldo et al. (Genome Research 6 (1996):791). |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25: 3389–3402. | ESTs: Probability value = 1.0E-8 or less Full Length sequences: Probability value = 1.0E-10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W. R. (1990) Methods Enzymol. 183: 63–98; and Smith, T. F. and M. S. Waterman (1981) Adv. Appl. Math. 2:482–489. | ESTs: fasta E value = 1.06E-6 Assembled ESTs: fasta Identity = 95% or greater and Match length = 200 bases or greater; fastx E. value = 1.0E-8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37: 417–424. | Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235:1501–1531; Sonnhammer, E. L. L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25: 217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |

TABLE 5-continued

| Program | Description | Reference | Parameter Threshold |
| --- | --- | --- | --- |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12: 431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. An isolated polypeptide selected from the group consisting of:
   a) a polypeptide comprising the amino acid sequence of SEQ ID NO:14,
   b) a polypeptide comprising a naturally occurring amino acid sequence at least 90% identical to the amino acid sequence of SEQ ID NO:14, said polypeptide having pyrroline-5-carboxylate reductase activity,
   c) a polypeptide comprising a polypeptide fragment, wherein the polypeptide fragment is a fragment of the amino acid sequence of SEQ ED NO:14, said polypeptide fragment having pyrroline-5-carboxylate reductase activity, and
   d) a polypeptide comprising an immunogenic fragment, wherein immunogenic fragment comprising at least 10 contiguous amino acid residues of the amino acid sequence of SEQ ID NO:14.

2. An isolated polypeptide of claim 1, comprising the amino acid sequence of SEQ ID NO:14.

3. An isolated polynucleotide encoding a polypeptide of claim 1.

4. An isolated polynucleotide encoding a polypeptide of claim 2.

5. An isolated polynucleotide of claim 4, having the sequence of SEQ ID NO:29.

6. A recombinant polynucleotide comprising a promoter sequence operably linked to a polynucleotide of claim 3.

7. A cell transformed with a recombinant polynucleotide of claim 6.

8. An isolated polynucleotide selected from the group consisting of:
   a) a polynucleotide comprising the polynucleotide sequence of SEQ ID NO:29,
   b) a polynucleotide comprising a natural occurring polynucleotide sequence at least 90% identical to the polynucleotide sequence of SEQ ID NO:29 encoding a polypeptide having pyrroline-5-carboxylate reductase activity,
   c) a polynucleotide comprising a polynucleotide sequence encoding a polypeptide fragment of SEQ ID NO:14 having pyrroline-5-carboxylate reductase activity,
   d) a polynucleotide complementary to the polynucleotide of a),
   e) a polynucleotide complementary to the polynucleotide of b), and
   f) a polynucleotide complementary to the polynucleotide of c), and
   g) an RNA equivalent of a)–f).

9. A method for detecting a target polynucleotide in a sample, the target polynucleotide having a sequence of a polynucleotide of claim 8, the method comprising:
   a) hybridizing the sample with a probe comprising at least 20 contiguous nucleotides comprising a sequence complementary to the target polynucleotide in the sample, and which probe specifically hybridizes to the target polynucleotide, under conditions whereby a hybridization complex is formed between the probe and the target polynucleotide or fragment thereof; and
   b) detecting the presence of the hybridization complex, wherein the presence of the hybridization complex correlates with presence of the target polynucleotide in the sample.

10. A method of detecting a target polynucleotide in a sample, the target polynucleotide having a sequence of a polynucleotide of claim 8, the method comprising:
   a) amplifying the target polynucleotide or fragment thereof using polymerase chain reaction amplification, and
   b) detecting the presence or absence of the amplified target polynucleotide or fragment thereof, and, optionally present, the amount thereof.

11. A method for producing a polypeptide encoded by a polynucleotide of claim 8, the method comprising:
   a) culturing a cell under conditions suitable for expression of the polypeptide, wherein the cell is transformed with a recombinant polynucleotide, and the recombinant polynucleotide comprises a promoter sequence operably linked to a polynucleotide of claim 8; and
   b) recovering the polypeptide so expressed.

12. A method of a screening a compound for effectivenss in altering expression of a target polynucleotide, wherein the target polynucleotide comprises a sequence of claim 8, the method comprising:
   a) exposing a sample comprising the target polynucleotide to a compound, under conditions suitable for the expression of the target polynucleotide,
   b) detecting altered expression of the target polynucleotide, and
   c) comparing the expression of the target polynucleotide in the presence of varying amounts of the compound and in the absence of the compound.

13. A method of assessing toxicity of a test compound, the method comprising:
   a) treating a biological sample containing nucleic with the test compound,
   b) hybridizing the nucleic acids of the treated biological sample with a probe comprising at least 20 contiguous nucleotides of a polynucleotide of claim 8 under conditions whereby a specific hybridization complex is formed between the probe and a target polynucleotide in the biological sample, the target polynucleotide comprising a polynucleotide sequence of a polynucleotide of claim 8 or fragment thereof,
   c) quantifying the amount of hybridization complex, and
   d) comparing the amount of hybridization complex in the treated biological sample with the amount of hybridization complex in an untreated biological sample, wherein a difference in the amount of hybridization complex in the treated biological sample indicates potential toxicity of the test compound.

14. A method of screening for a compound that modulates the activity of the polypeptide of claim 1, the method comprising:
   a) combining polypeptide of claim 1 with at least one test compound under conditions permissive for the activity of the polypeptide of claim 1,
   b) assessing the activity of the polypeptide of claim 1 in the presence of the test compound, and
   c) comparing the activity of the polypeptide of claim 1 in the presence of the test compound with the activity of the polypeptide of claim 1 in the absence of the test compound, wherein a change in the activity of the polypeptide of claim 1 in the presence of the test compound is indicative of a compound that modulates the activity of the polypeptide of claim 1.

* * * * *

SEQUENCE LISTING

<160> NUMBER OF SEQ ID NOS: 30

<210> SEQ ID NO 1
<211> LENGTH: 280
<212> TYPE: PRT
<213> ORGANISM: Homo sapiens
<220> FEATURE:
<221> NAME/KEY: misc_feature
<223> OTHER INFORMATION: Incyte ID No.: 000746CD1

<400> SEQUENCE: 1

```
Met Ala Pro Ser Gly Ser Leu Ala Val Pro Leu Ala Val Leu Val
 1               5                  10                  15

Leu Leu Leu Trp Gly Ala Pro Trp Thr His Gly Arg Arg Ser Asn
                20                  25                  30

Val Arg Val Ile Thr Asp Glu Asn Trp Arg Glu Leu Leu Glu Gly
                35                  40                  45

Asp Trp Met Ile Glu Phe Tyr Ala Pro Trp Cys Pro Ala Cys Gln
                50                  55                  60

Asn Leu Gln Pro Glu Trp Glu Ser Phe Ala Glu Trp Gly Glu Asp
                65                  70                  75

Leu Glu Val Asn Ile Ala Lys Val Asp Val Thr Glu Gln Pro Gly
                80                  85                  90

Leu Ser Gly Arg Phe Ile Ile Thr Ala Leu Pro Thr Ile Tyr His
                95                 100                 105

Cys Lys Asp Gly Glu Phe Arg Arg Tyr Gln Gly Pro Arg Thr Lys
               110                 115                 120

Lys Asp Phe Ile Asn Phe Ile Ser Asp Lys Glu Trp Lys Ser Ile
               125                 130                 135

Glu Pro Val Ser Ser Trp Phe Gly Pro Gly Ser Val Leu Met Ser
               140                 145                 150

Ser Met Ser Ala Leu Phe Gln Leu Ser Met Trp Ile Arg Thr Cys
               155                 160                 165

His Asn Tyr Phe Ile Glu Asp Leu Gly Leu Pro Val Trp Gly Ser
               170                 175                 180

Tyr Thr Val Phe Ala Leu Ala Thr Leu Phe Ser Gly Leu Leu Leu
               185                 190                 195

Gly Leu Cys Met Ile Phe Val Ala Asp Cys Leu Cys Pro Ser Lys
```

-continued

```
                200                 205                 210
Arg Arg Arg Pro Gln Pro Tyr Pro Tyr Pro Ser Lys Lys Leu Leu
                215                 220                 225

Ser Glu Ser Ala Gln Pro Leu Lys Lys Val Glu Glu Glu Gln Glu
                230                 235                 240

Ala Asp Glu Glu Asp Val Ser Glu Glu Ala Glu Ser Lys Glu
                245                 250                 255

Gly Thr Asn Lys Asp Phe Pro Gln Asn Ala Ile Arg Gln Arg Ser
                260                 265                 270

Leu Gly Pro Ser Leu Ala Thr Asp Lys Ser
                275                 280

<210> SEQ ID NO 2
<211> LENGTH: 166
<212> TYPE: PRT
<213> ORGANISM: Homo sapiens
<220> FEATURE:
<221> NAME/KEY: misc_feature
<223> OTHER INFORMATION: Incyte ID No.: 2472577CD1

<400> SEQUENCE: 2

Met Gln Glu Ile Asn Gln Asn Leu Ala Glu Glu Ala Gly Leu Asn
 1               5                  10                  15

Ile Thr His Ile Cys Leu Pro Pro Asp Ser Glu Ala Glu Ile
                20                  25                  30

Ile Asp Glu Ile Leu Lys Ile Asn Glu Asp Thr Arg Val His Gly
                35                  40                  45

Leu Ala Leu Gln Ile Ser Glu Asn Leu Phe Ser Asn Lys Val Leu
                50                  55                  60

Asn Ala Leu Lys Pro Glu Lys Asp Val Asp Gly Val Thr Asp Ile
                65                  70                  75

Asn Leu Gly Lys Leu Val Arg Gly Asp Ala His Glu Cys Phe Val
                80                  85                  90

Ser Pro Val Ala Lys Ala Val Ile Glu Leu Leu Glu Lys Ser Val
                95                  100                 105

Gly Val Asn Leu Asp Gly Lys Lys Ile Leu Val Val Gly Ala His
                110                 115                 120

Gly Ser Leu Glu Ala Ala Leu Gln Cys Leu Phe Gln Arg Lys Gly
                125                 130                 135

Ser Met Thr Met Ser Ile Gln Trp Lys Thr Arg Gln Leu Gln Ser
                140                 145                 150

Lys Thr Glu Ser Arg Ser Val Thr Arg Leu Glu Cys Arg Arg Val
                155                 160                 165

Ile

<210> SEQ ID NO 3
<211> LENGTH: 319
<212> TYPE: PRT
<213> ORGANISM: Homo sapiens
<220> FEATURE:
<221> NAME/KEY: misc_feature
<223> OTHER INFORMATION: Incyte ID No.: 2160405CD1

<400> SEQUENCE: 3

Met Ala Ser Ser Ala Ala Gly Cys Val Val Ile Val Gly Ser Gly
 1               5                  10                  15

Val Ile Gly Arg Ser Trp Ala Met Leu Phe Ala Ser Gly Gly Phe
                20                  25                  30
```

-continued

```
Gln Val Lys Leu Tyr Asp Ile Glu Gln Gln Ile Arg Asn Ala
             35                  40                  45

Leu Glu Asn Ile Arg Lys Glu Met Lys Leu Leu Glu Gln Ala Gly
         50                  55                  60

Ser Leu Lys Gly Ser Leu Ser Val Glu Glu Gln Leu Ser Leu Ile
     65                  70                  75

Ser Gly Cys Pro Asn Ile Gln Glu Ala Val Glu Gly Ala Met His
 80                  85                  90

Ile Gln Glu Cys Val Pro Glu Asp Leu Glu Leu Lys Lys Ile
         95                  100                 105

Phe Ala Gln Leu Asp Ser Ile Ile Asp Asp Arg Val Ile Leu Ser
             110                 115                 120

Ser Ser Thr Ser Cys Leu Met Pro Ser Lys Leu Phe Ala Gly Leu
         125                 130                 135

Val His Val Lys Gln Cys Ile Val Ala His Pro Val Asn Pro Pro
     140                 145                 150

Tyr Tyr Ile Pro Leu Val Glu Leu Val Pro His Pro Glu Thr Ala
 155                 160                 165

Pro Thr Thr Val Asp Arg Thr His Ala Leu Met Lys Lys Ile Gly
             170                 175                 180

Gln Cys Pro Met Arg Val Gln Lys Glu Val Ala Gly Phe Val Leu
         185                 190                 195

Asn Arg Leu Gln Tyr Ala Ile Ile Ser Glu Ala Trp Arg Leu Val
     200                 205                 210

Glu Glu Gly Ile Val Ser Pro Ser Asp Leu Asp Leu Val Met Ser
 215                 220                 225

Glu Gly Leu Gly Met Arg Tyr Ala Phe Ile Gly Pro Leu Glu Thr
             230                 235                 240

Met His Leu Asn Ala Glu Gly Met Leu Ser Tyr Cys Asp Arg Tyr
         245                 250                 255

Ser Glu Gly Ile Lys His Val Leu Gln Thr Phe Gly Pro Ile Pro
     260                 265                 270

Glu Phe Ser Arg Ala Thr Ala Glu Lys Val Asn Gln Asp Met Cys
 275                 280                 285

Met Lys Val Pro Asp Asp Pro Glu His Leu Ala Ala Arg Arg Gln
             290                 295                 300

Trp Arg Asp Glu Cys Leu Met Arg Leu Ala Lys Leu Lys Ser Gln
         305                 310                 315

Val Gln Pro Gln
```

<210> SEQ ID NO 4
<211> LENGTH: 318
<212> TYPE: PRT
<213> ORGANISM: Homo sapiens
<220> FEATURE:
<221> NAME/KEY: misc_feature
<223> OTHER INFORMATION: Incyte ID No.: 2591695CD1

<400> SEQUENCE: 4

```
Met Ala Pro Trp Ala Glu Ala Glu His Ser Ala Leu Asn Pro Leu
 1               5                  10                  15

Arg Ala Val Trp Leu Thr Leu Thr Ala Ala Phe Leu Leu Thr Leu
             20                  25                  30

Leu Leu Gln Leu Leu Pro Pro Gly Leu Leu Pro Gly Cys Ala Ile
         35                  40                  45
```

-continued

```
Phe Gln Asp Leu Ile Arg Tyr Gly Lys Thr Lys Cys Gly Glu Pro
                 50                  55                  60

Ser Arg Pro Ala Ala Cys Arg Ala Phe Asp Val Pro Lys Arg Tyr
             65                  70                  75

Phe Ser His Phe Tyr Ile Ile Ser Val Leu Trp Asn Gly Phe Leu
             80                  85                  90

Leu Trp Cys Leu Thr Gln Ser Leu Phe Leu Gly Ala Pro Phe Pro
             95                 100                 105

Ser Trp Leu His Gly Leu Leu Arg Ile Leu Gly Ala Ala Gln Phe
            110                 115                 120

Gln Gly Gly Glu Leu Ala Leu Ser Ala Phe Leu Val Leu Val Phe
            125                 130                 135

Leu Trp Leu His Ser Leu Arg Arg Leu Phe Glu Cys Leu Tyr Val
            140                 145                 150

Ser Val Phe Ser Asn Val Met Ile His Val Gln Tyr Cys Phe
            155                 160                 165

Gly Leu Val Tyr Tyr Val Leu Val Gly Leu Thr Val Leu Ser Gln
            170                 175                 180

Val Pro Met Asp Gly Arg Asn Ala Tyr Ile Thr Gly Lys Asn Leu
            185                 190                 195

Leu Met Gln Ala Arg Trp Phe His Ile Leu Gly Met Met Met Phe
            200                 205                 210

Ile Trp Ser Ser Ala His Gln Tyr Lys Cys His Val Ile Leu Gly
            215                 220                 225

Asn Leu Arg Lys Asn Lys Ala Gly Val Val Ile His Cys Asn His
            230                 235                 240

Arg Ile Pro Phe Gly Asp Trp Phe Glu Tyr Val Ser Ser Pro Asn
            245                 250                 255

Tyr Leu Ala Glu Leu Met Ile Tyr Val Ser Met Ala Val Thr Phe
            260                 265                 270

Gly Phe His Asn Leu Thr Trp Trp Leu Val Val Thr Asn Val Phe
            275                 280                 285

Phe Asn Gln Ala Leu Ser Ala Phe Leu Ser His Gln Phe Tyr Lys
            290                 295                 300

Ser Lys Phe Val Ser Tyr Pro Lys His Arg Lys Ala Phe Leu Pro
            305                 310                 315

Phe Leu Phe

<210> SEQ ID NO 5
<211> LENGTH: 330
<212> TYPE: PRT
<213> ORGANISM: Homo sapiens
<220> FEATURE:
<221> NAME/KEY: misc_feature
<223> OTHER INFORMATION: Incyte ID No.: 474100CD1

<400> SEQUENCE: 5

Met Pro Glu Met Pro Glu Asp Met Glu Gln Glu Glu Val Asn Ile
  1               5                  10                  15

Pro Asn Arg Arg Val Leu Val Thr Gly Ala Thr Gly Leu Leu Gly
             20                  25                  30

Arg Ala Val His Lys Glu Phe Gln Gln Asn Asn Trp His Ala Val
             35                  40                  45

Gly Cys Gly Phe Arg Arg Ala Arg Pro Lys Phe Glu Gln Val Asn
             50                  55                  60
```

-continued

```
Leu Leu Asp Ser Asn Ala Val His His Ile Ile His Asp Phe Gln
             65                  70                  75

Pro His Val Ile Val His Cys Ala Ala Glu Arg Arg Pro Asp Val
             80                  85                  90

Val Glu Asn Gln Pro Asp Ala Ala Ser Gln Leu Asn Val Asp Ala
             95                 100                 105

Ser Gly Asn Leu Ala Lys Glu Ala Asp Phe Phe Phe Phe Phe Val
            110                 115                 120

Ala Ala Val Gly Ala Phe Leu Ile Tyr Ile Ser Ser Asp Tyr Val
            125                 130                 135

Phe Asp Gly Thr Asn Pro Pro Tyr Arg Glu Glu Asp Ile Pro Ala
            140                 145                 150

Pro Leu Asn Leu Tyr Gly Lys Thr Lys Leu Asp Gly Glu Lys Ala
            155                 160                 165

Val Leu Glu Asn Asn Leu Gly Ala Ala Val Leu Arg Ile Pro Ile
            170                 175                 180

Leu Tyr Gly Glu Val Glu Lys Leu Glu Glu Ser Ala Val Thr Val
            185                 190                 195

Met Phe Asp Lys Val Arg Phe Ser Asn Lys Ser Ala Asn Met Asp
            200                 205                 210

His Trp Gln Gln Arg Phe Pro Thr His Val Lys Asp Val Ala Thr
            215                 220                 225

Val Cys Arg Gln Leu Ala Glu Lys Arg Met Leu Asp Pro Ser Ile
            230                 235                 240

Lys Gly Thr Phe His Trp Ser Gly Asn Glu Gln Met Thr Lys Tyr
            245                 250                 255

Glu Met Ala Cys Ala Ile Ala Asp Ala Phe Asn Leu Pro Ser Ser
            260                 265                 270

His Leu Arg Pro Ile Thr Asp Ser Pro Val Leu Gly Ala Gln Arg
            275                 280                 285

Pro Arg Asn Ala Gln Leu Asp Cys Ser Lys Leu Glu Thr Leu Gly
            290                 295                 300

Ile Gly Gln Arg Thr Pro Phe Arg Ile Gly Ile Lys Glu Ser Leu
            305                 310                 315

Trp Pro Phe Leu Ile Asp Lys Arg Trp Arg Gln Thr Val Phe His
            320                 325                 330

<210> SEQ ID NO 6
<211> LENGTH: 266
<212> TYPE: PRT
<213> ORGANISM: Homo sapiens
<220> FEATURE:
<221> NAME/KEY: misc_feature
<223> OTHER INFORMATION: Incyte ID No.: 1304767CD1

<400> SEQUENCE: 6

Met Ala Thr Gly Thr Arg Tyr Ala Gly Lys Val Val Val Val Thr
  1               5                  10                  15

Gly Ile Gly Ala Gly Ile Val Arg Ala Phe Val Asp Ser Gly Ala
             20                  25                  30

Arg Val Val Ile Cys Asp Lys Asp Glu Ser Gly Gly Arg Ala Leu
             35                  40                  45

Glu Gln Glu Leu Pro Gly Ala Val Phe Ile Leu Cys Asp Val Thr
             50                  55                  60

Gln Glu Asp Asp Val Lys Thr Leu Val Ser Glu Thr Ile Arg Arg
```

```
                65                  70                  75
Phe Gly Arg Leu Asp Cys Val Val Asn Asn Ala Gly His His Pro
                    80                  85                  90
Pro Pro Gln Arg Pro Glu Glu Thr Ser Ala Gln Gly Phe Arg Gln
                    95                 100                 105
Leu Leu Glu Leu Asn Leu Leu Gly Thr Tyr Thr Leu Thr Lys Leu
                   110                 115                 120
Ala Leu Pro Tyr Leu Arg Lys Ser Gln Gly Asn Val Ile Asn Ile
                   125                 130                 135
Ser Ser Leu Val Gly Ala Ile Gly Gln Ala Gln Ala Val Pro Tyr
                   140                 145                 150
Val Ala Thr Lys Gly Ala Val Thr Ala Met Thr Lys Ala Leu Ala
                   155                 160                 165
Leu Asp Glu Ser Pro Tyr Gly Val Arg Val Asn Cys Ile Ser Pro
                   170                 175                 180
Gly Asn Ile Trp Thr Pro Leu Trp Glu Glu Leu Ala Ala Leu Met
                   185                 190                 195
Pro Asp Pro Arg Ala Thr Ile Arg Glu Gly Met Leu Ala Gln Pro
                   200                 205                 210
Leu Gly Arg Met Gly Gln Pro Ala Glu Val Gly Ala Ala Ala Val
                   215                 220                 225
Phe Leu Ala Ser Glu Ala Asn Phe Cys Thr Gly Ile Glu Leu Leu
                   230                 235                 240
Val Thr Gly Gly Ala Glu Leu Gly Tyr Gly Cys Lys Ala Ser Arg
                   245                 250                 255
Ser Thr Pro Val Asp Ala Pro Asp Ile Pro Ser
                   260                 265
```

<210> SEQ ID NO 7
<211> LENGTH: 302
<212> TYPE: PRT
<213> ORGANISM: Homo sapiens
<220> FEATURE:
<221> NAME/KEY: misc_feature
<223> OTHER INFORMATION: Incyte ID No.: 1465978CD1

<400> SEQUENCE: 7

```
Met Val Trp Lys Arg Leu Gly Ala Leu Val Met Phe Pro Leu Gln
  1               5                  10                  15
Met Ile Tyr Leu Val Val Lys Ala Ala Val Gly Leu Val Leu Pro
                    20                  25                  30
Ala Lys Leu Arg Asp Leu Ser Arg Glu Asn Val Leu Ile Thr Gly
                    35                  40                  45
Gly Gly Arg Gly Ile Gly Arg Gln Leu Ala Arg Glu Phe Ala Glu
                    50                  55                  60
Arg Gly Ala Arg Lys Ile Val Leu Trp Gly Arg Thr Glu Lys Cys
                    65                  70                  75
Leu Lys Glu Thr Thr Glu Glu Ile Arg Gln Met Gly Thr Glu Cys
                    80                  85                  90
His Tyr Phe Ile Cys Asp Val Gly Asn Arg Glu Glu Val Tyr Gln
                    95                 100                 105
Thr Ala Lys Ala Val Arg Glu Lys Val Gly Asp Ile Thr Ile Leu
                   110                 115                 120
Val Asn Asn Ala Ala Val Val His Gly Lys Ser Leu Met Asp Ser
                   125                 130                 135
```

-continued

```
Asp Asp Asp Ala Leu Leu Lys Ser Gln His Ile Asn Thr Leu Gly
            140                 145                 150

Gln Phe Trp Thr Thr Lys Ala Phe Leu Pro Arg Met Leu Glu Leu
            155                 160                 165

Gln Asn Gly His Ile Val Cys Leu Asn Ser Val Leu Ala Leu Ser
            170                 175                 180

Ala Ile Pro Gly Ala Ile Asp Tyr Cys Thr Ser Lys Ala Ser Ala
            185                 190                 195

Phe Ala Phe Met Glu Ser Leu Thr Leu Gly Leu Leu Asp Cys Pro
            200                 205                 210

Gly Val Ser Ala Thr Thr Val Leu Pro Phe His Thr Ser Thr Glu
            215                 220                 225

Met Phe Gln Gly Met Arg Val Arg Phe Pro Asn Leu Phe Pro Pro
            230                 235                 240

Leu Lys Pro Glu Thr Val Ala Arg Arg Thr Val Glu Ala Val Gln
            245                 250                 255

Leu Asn Gln Ala Leu Leu Leu Pro Trp Thr Met His Ala Leu
            260                 265                 270

Val Ile Leu Lys Ser Ile Leu Pro Gln Ala Ala Leu Glu Glu Ile
            275                 280                 285

His Lys Phe Ser Gly Thr Tyr Thr Cys Met Asn Thr Phe Lys Gly
            290                 295                 300

Arg Thr
```

<210> SEQ ID NO 8
<211> LENGTH: 300
<212> TYPE: PRT
<213> ORGANISM: Homo sapiens
<220> FEATURE:
<221> NAME/KEY: misc_feature
<223> OTHER INFORMATION: Incyte ID No.: 1635966CD1

<400> SEQUENCE: 8

```
Met Lys Phe Leu Leu Asp Ile Leu Leu Leu Pro Leu Leu Ile
  1               5                  10                  15

Val Cys Ser Leu Glu Ser Phe Val Lys Leu Phe Ile Pro Lys Arg
             20                  25                  30

Arg Lys Ser Val Thr Gly Glu Ile Val Leu Ile Thr Gly Ala Gly
             35                  40                  45

His Gly Ile Val Arg Leu Thr Ala Tyr Glu Phe Ala Lys Leu Lys
             50                  55                  60

Ser Lys Leu Val Leu Trp Asp Ile Asn Lys His Gly Leu Glu Glu
             65                  70                  75

Thr Ala Ala Lys Cys Lys Gly Leu Gly Ala Lys Val His Thr Phe
             80                  85                  90

Val Val Asp Cys Ser Asn Arg Glu Asp Ile Tyr Ser Ser Ala Lys
             95                 100                 105

Lys Val Lys Ala Glu Ile Gly Asp Val Ser Ile Leu Val Asn Asn
            110                 115                 120

Ala Gly Val Val Tyr Thr Ser Asp Leu Phe Ala Thr Gln Asp Pro
            125                 130                 135

Gln Ile Glu Lys Thr Phe Glu Val Asn Val Leu Ala His Phe Trp
            140                 145                 150

Thr Thr Lys Ala Phe Leu Pro Ala Met Thr Lys Asn Asn His Gly
            155                 160                 165
```

-continued

```
His Ile Val Thr Val Ala Ser Ala Ala Gly His Val Ser Val Pro
            170                 175                 180

Phe Leu Leu Ala Tyr Cys Ser Ser Lys Phe Ala Ala Val Gly Phe
            185                 190                 195

His Lys Thr Leu Thr Asp Glu Leu Ala Ala Leu Gln Ile Thr Gly
            200                 205                 210

Val Lys Thr Thr Cys Leu Cys Pro Asn Phe Val Asn Thr Gly Phe
            215                 220                 225

Ile Lys Asn Pro Ser Thr Ser Leu Gly Pro Thr Leu Glu Pro Glu
            230                 235                 240

Glu Val Val Asn Arg Leu Met His Gly Ile Leu Thr Glu Gln Lys
            245                 250                 255

Met Ile Phe Ile Pro Ser Ser Ile Ala Phe Leu Thr Thr Leu Glu
            260                 265                 270

Arg Ile Leu Pro Glu Arg Phe Leu Ala Val Leu Lys Arg Lys Ile
            275                 280                 285

Ser Val Lys Phe Asp Ala Val Ile Gly Tyr Lys Met Lys Ala Gln
            290                 295                 300

<210> SEQ ID NO 9
<211> LENGTH: 613
<212> TYPE: PRT
<213> ORGANISM: Homo sapiens
<220> FEATURE:
<221> NAME/KEY: misc_feature
<223> OTHER INFORMATION: Incyte ID No.: 1638410CD1

<400> SEQUENCE: 9

Met Phe Arg Cys Gly Gly Leu Ala Ala Gly Ala Leu Lys Gln Lys
  1               5                  10                  15

Leu Val Pro Leu Val Arg Thr Val Cys Val Arg Ser Pro Arg Gln
             20                  25                  30

Arg Asn Arg Leu Pro Gly Asn Leu Phe Gln Arg Trp His Val Pro
             35                  40                  45

Leu Glu Leu Gln Met Thr Arg Gln Met Ala Ser Ser Gly Ala Ser
             50                  55                  60

Gly Gly Lys Ile Asp Asn Ser Val Leu Val Leu Ile Val Gly Leu
             65                  70                  75

Ser Thr Val Gly Ala Gly Ala Tyr Ala Tyr Lys Thr Met Lys Glu
             80                  85                  90

Asp Glu Lys Arg Tyr Asn Glu Arg Ile Ser Gly Leu Gly Leu Thr
             95                 100                 105

Pro Glu Gln Lys Gln Lys Lys Ala Ala Leu Ser Ala Ser Glu Gly
            110                 115                 120

Glu Glu Val Pro Gln Asp Lys Ala Pro Ser His Val Pro Phe Leu
            125                 130                 135

Leu Ile Gly Gly Gly Thr Ala Ala Phe Ala Ala Ala Arg Ser Ile
            140                 145                 150

Arg Ala Arg Asp Pro Gly Ala Arg Val Leu Ile Val Ser Glu Asp
            155                 160                 165

Pro Glu Leu Pro Tyr Met Arg Pro Pro Leu Ser Lys Glu Leu Trp
            170                 175                 180

Phe Ser Asp Asp Pro Asn Val Thr Lys Thr Leu Arg Phe Lys Gln
            185                 190                 195

Trp Asn Gly Lys Glu Arg Ser Ile Tyr Phe Gln Pro Pro Ser Phe
            200                 205                 210
```

-continued

```
Tyr Val Ser Ala Gln Asp Leu Pro His Ile Glu Asn Gly Gly Val
            215                 220                 225

Ala Val Leu Thr Gly Lys Lys Val Gln Leu Asp Val Arg Asp
            230                 235                 240

Asn Met Val Lys Leu Asn Asp Gly Ser Gln Ile Thr Tyr Glu Lys
            245                 250                 255

Cys Leu Ile Ala Thr Gly Gly Thr Pro Arg Ser Leu Ser Ala Ile
            260                 265                 270

Asp Arg Ala Gly Ala Glu Val Lys Ser Arg Thr Thr Leu Phe Arg
            275                 280                 285

Lys Ile Gly Asp Phe Arg Ser Leu Glu Lys Ile Ser Arg Glu Val
            290                 295                 300

Lys Ser Ile Thr Ile Gly Gly Phe Leu Gly Ser Glu Leu
            305                 310                 315

Ala Cys Ala Leu Gly Arg Lys Ala Arg Ala Leu Gly Thr Glu Val
            320                 325                 330

Ile Gln Leu Phe Pro Glu Lys Gly Asn Met Gly Lys Ile Leu Pro
            335                 340                 345

Glu Tyr Leu Ser Asn Trp Thr Met Glu Lys Val Arg Arg Glu Gly
            350                 355                 360

Val Lys Val Met Pro Asn Ala Ile Val Gln Ser Val Gly Val Ser
            365                 370                 375

Ser Gly Lys Leu Leu Ile Lys Leu Lys Asp Gly Arg Lys Val Glu
            380                 385                 390

Thr Asp His Ile Val Ala Ala Val Gly Leu Glu Pro Asn Val Glu
            395                 400                 405

Leu Ala Lys Thr Gly Gly Leu Glu Ile Asp Ser Asp Phe Gly Gly
            410                 415                 420

Phe Arg Val Asn Ala Glu Leu Gln Ala Arg Ser Asn Ile Trp Val
            425                 430                 435

Ala Gly Asp Ala Ala Cys Phe Tyr Asp Ile Lys Leu Gly Arg Arg
            440                 445                 450

Arg Val Glu His His Asp His Ala Val Val Ser Gly Arg Leu Ala
            455                 460                 465

Gly Glu Asn Met Thr Gly Ala Ala Lys Pro Tyr Trp His Gln Ser
            470                 475                 480

Met Phe Trp Ser Asp Leu Gly Pro Asp Val Gly Tyr Glu Ala Ile
            485                 490                 495

Gly Leu Val Asp Ser Ser Leu Pro Thr Val Gly Val Phe Ala Lys
            500                 505                 510

Ala Thr Ala Gln Asp Asn Pro Lys Ser Ala Thr Glu Gln Ser Gly
            515                 520                 525

Thr Gly Ile Arg Ser Glu Ser Glu Thr Glu Ser Glu Ala Ser Glu
            530                 535                 540

Ile Thr Ile Pro Pro Ser Thr Pro Ala Val Pro Gln Ala Pro Val
            545                 550                 555

Gln Gly Glu Asp Tyr Gly Lys Gly Val Ile Phe Tyr Leu Arg Asp
            560                 565                 570

Lys Val Val Val Gly Ile Val Leu Trp Asn Ile Phe Asn Arg Met
            575                 580                 585

Pro Ile Ala Arg Lys Ile Ile Lys Asp Gly Glu Gln His Glu Asp
            590                 595                 600
```

-continued

Leu Asn Glu Val Ala Lys Leu Phe Asn Ile His Glu Asp
            605                 610

<210> SEQ ID NO 10
<211> LENGTH: 325
<212> TYPE: PRT
<213> ORGANISM: Homo sapiens
<220> FEATURE:
<221> NAME/KEY: misc_feature
<223> OTHER INFORMATION: Incyte ID No.: 1743409CD1

<400> SEQUENCE: 10

Met Val Ser Pro Ala Thr Arg Lys Ser Leu Pro Lys Val Lys Ala
  1               5                  10                  15

Met Asp Phe Ile Thr Ser Thr Ala Ile Leu Pro Leu Leu Phe Gly
                 20                  25                  30

Cys Leu Gly Val Phe Gly Leu Phe Arg Leu Leu Gln Trp Val Arg
                 35                  40                  45

Gly Lys Ala Tyr Leu Arg Asn Ala Val Val Ile Thr Gly Ala
                 50                  55                  60

Thr Ser Gly Leu Gly Lys Glu Cys Ala Lys Val Phe Tyr Ala Ala
                 65                  70                  75

Gly Ala Lys Leu Val Leu Cys Gly Arg Asn Gly Gly Ala Leu Glu
                 80                  85                  90

Glu Leu Ile Arg Glu Leu Thr Ala Ser His Ala Thr Lys Val Gln
                 95                 100                 105

Thr His Lys Pro Tyr Leu Val Thr Phe Asp Leu Thr Asp Ser Gly
                110                 115                 120

Ala Ile Val Ala Ala Ala Glu Ile Leu Gln Cys Phe Gly Tyr
                125                 130                 135

Val Asp Ile Leu Val Asn Asn Ala Gly Ile Ser Tyr Arg Gly Thr
                140                 145                 150

Ile Met Asp Thr Thr Val Asp Val Asp Lys Arg Val Met Glu Thr
                155                 160                 165

Asn Tyr Phe Gly Pro Val Ala Leu Thr Lys Ala Leu Leu Pro Ser
                170                 175                 180

Met Ile Lys Arg Arg Gln Gly His Ile Val Ala Ile Ser Ser Ile
                185                 190                 195

Gln Gly Lys Met Ser Ile Pro Phe Arg Ser Ala Tyr Ala Ala Ser
                200                 205                 210

Lys His Ala Thr Gln Ala Phe Phe Asp Cys Leu Arg Ala Glu Met
                215                 220                 225

Glu Gln Tyr Glu Ile Glu Val Thr Val Ile Ser Pro Gly Tyr Ile
                230                 235                 240

His Thr Asn Leu Ser Val Asn Ala Ile Thr Ala Asp Gly Ser Arg
                245                 250                 255

Tyr Gly Val Met Asp Thr Thr Thr Ala Gln Gly Arg Ser Pro Val
                260                 265                 270

Glu Val Ala Gln Asp Val Leu Ala Ala Val Gly Lys Lys Lys Lys
                275                 280                 285

Asp Val Ile Leu Ala Asp Leu Leu Pro Ser Leu Ala Val Tyr Leu
                290                 295                 300

Arg Thr Leu Ala Pro Gly Leu Phe Phe Ser Leu Met Ala Ser Arg
                305                 310                 315

Ala Arg Lys Glu Arg Lys Ser Lys Asn Ser
                320                 325

-continued

<210> SEQ ID NO 11
<211> LENGTH: 421
<212> TYPE: PRT
<213> ORGANISM: Homo sapiens
<220> FEATURE:
<221> NAME/KEY: misc_feature
<223> OTHER INFORMATION: Incyte ID No.: 1803830CD1

<400> SEQUENCE: 11

```
Met Trp Tyr His Arg Leu Ser His Leu His Ser Arg Leu Gln Asp
 1               5                  10                  15

Leu Leu Lys Gly Gly Val Ile Tyr Pro Ala Leu Pro Gln Pro Asn
                20                  25                  30

Phe Lys Ser Leu Leu Pro Leu Ala Val His Trp His His Thr Ala
                35                  40                  45

Ser Lys Ser Leu Thr Cys Ala Trp Gln Gln His Glu Asp His Phe
                50                  55                  60

Glu Leu Lys Tyr Ala Asn Thr Val Met Arg Leu Asp Tyr Val Trp
                65                  70                  75

Leu Arg Asp His Cys Arg Ser Ala Ser Cys Tyr Asn Ser Lys Thr
                80                  85                  90

His Gln Arg Ser Trp Asp Thr Ala Ser Val Asp Leu Cys Ile Lys
                95                 100                 105

Pro Lys Thr Ile Arg Leu Asp Glu Thr Thr Leu Phe Phe Thr Trp
               110                 115                 120

Pro Asp Gly His Val Thr Lys Tyr Asp Leu Asn Trp Leu Val Lys
               125                 130                 135

Asn Ser Tyr Glu Gly Gln Lys Gln Lys Val Ile Gln Pro Arg Ile
               140                 145                 150

Leu Trp Asn Ala Glu Ile Tyr Gln Gln Ala Gln Val Pro Ser Val
               155                 160                 165

Asp Cys Gln Ser Phe Leu Glu Thr Asn Glu Gly Leu Lys Lys Phe
               170                 175                 180

Leu Gln Asn Phe Leu Leu Tyr Gly Ile Ala Phe Val Glu Asn Val
               185                 190                 195

Pro Pro Thr Gln Glu His Thr Glu Lys Leu Ala Glu Arg Ile Ser
               200                 205                 210

Leu Ile Arg Glu Thr Ile Tyr Gly Arg Met Trp Tyr Phe Thr Ser
               215                 220                 225

Asp Phe Ser Arg Gly Asp Thr Ala Tyr Thr Lys Leu Ala Leu Asp
               230                 235                 240

Arg His Thr Asp Thr Thr Tyr Phe Gln Glu Pro Cys Gly Ile Gln
               245                 250                 255

Val Phe His Cys Leu Lys His Glu Gly Thr Gly Gly Arg Thr Leu
               260                 265                 270

Leu Val Asp Gly Phe Tyr Ala Ala Glu Gln Val Leu Gln Lys Ala
               275                 280                 285

Pro Glu Glu Phe Glu Leu Leu Ser Lys Val Pro Leu Lys His Glu
               290                 295                 300

Tyr Ile Glu Asp Val Gly Glu Cys His Asn His Met Ile Gly Ile
               305                 310                 315

Gly Pro Val Leu Asn Ile Tyr Pro Trp Asn Lys Glu Leu Tyr Leu
               320                 325                 330

Ile Arg Tyr Asn Asn Tyr Asp Arg Ala Val Ile Asn Thr Val Pro
```

-continued

```
                335                 340                 345
Tyr Asp Val Val His Arg Trp Tyr Thr Ala His Arg Thr Leu Thr
                350                 355                 360

Ile Glu Leu Arg Arg Pro Glu Asn Glu Phe Trp Val Lys Leu Lys
                365                 370                 375

Pro Gly Arg Val Leu Phe Ile Asp Asn Trp Arg Val Leu His Gly
                380                 385                 390

Arg Glu Cys Phe Thr Gly Tyr Arg Gln Leu Cys Gly Cys Tyr Leu
                395                 400                 405

Thr Arg Asp Asp Val Leu Asn Thr Ala Arg Leu Leu Gly Leu Gln
                410                 415                 420

Ala

SEQ ID NO 12
LENGTH: 610
TYPE: PRT
ORGANISM: Homo sapiens
FEATURE:
NAME/KEY: misc_feature
OTHER INFORMATION: Incyte ID No.: 1867333CD1

SEQUENCE: 12

Met Trp Leu Pro Leu Val Leu Leu Ala Val Leu Leu Ala
 1               5                  10                  15

Val Leu Cys Lys Val Tyr Leu Gly Leu Phe Ser Gly Ser Ser Pro
                20                  25                  30

Asn Pro Phe Ser Glu Asp Val Lys Arg Pro Pro Ala Pro Leu Val
                35                  40                  45

Thr Asp Lys Glu Ala Arg Lys Lys Val Leu Lys Gln Ala Phe Ser
                50                  55                  60

Ala Asn Gln Val Pro Glu Lys Leu Asp Val Val Ile Gly Ser
                65                      70                  75

Gly Phe Gly Gly Leu Ala Ala Ala Ile Leu Ala Lys Ala Gly
                80                      85                  90

Lys Arg Val Leu Val Leu Glu Gln His Thr Lys Ala Gly Gly Cys
                95                  100                 105

Cys His Thr Phe Gly Lys Asn Gly Leu Glu Phe Asp Thr Gly Ile
                110                 115                 120

His Tyr Ile Gly Arg Met Glu Glu Gly Ser Ile Gly Arg Phe Ile
                125                 130                 135

Leu Asp Gln Ile Thr Glu Gly Gln Leu Asp Trp Ala Pro Leu Ser
                140                 145                 150

Ser Pro Phe Asp Ile Met Val Leu Glu Gly Pro Asn Gly Arg Lys
                155                 160                 165

Glu Tyr Pro Met Tyr Ser Gly Glu Lys Ala Tyr Ile Gln Gly Leu
                170                 175                 180

Lys Glu Lys Phe Pro Gln Glu Glu Ala Ile Ile Asp Lys Tyr Ile
                185                 190                 195

Lys Leu Val Lys Val Ser Ser Gly Ala Pro His Ala Ile Leu
                200                 205                 210

Leu Lys Phe Leu Pro Leu Pro Val Val Gln Leu Leu Asp Arg Cys
                215                 220                 225

Gly Leu Leu Thr Arg Phe Ser Pro Phe Leu Gln Ala Ser Thr Gln
                230                 235                 240

Ser Leu Ala Glu Val Leu Gln Gln Leu Gly Ala Ser Ser Glu Leu
```

-continued

```
                245                 250                 255
Gln Ala Val Leu Ser Tyr Ile Phe Pro Thr Tyr Gly Val Thr Pro
            260                 265                 270
Asn His Ser Ala Phe Ser Met His Ala Leu Leu Val Asn His Tyr
        275                 280                 285
Met Lys Gly Gly Phe Tyr Pro Arg Gly Ser Ser Glu Ile Ala
        290                 295                 300
Phe His Thr Ile Pro Val Ile Gln Arg Ala Gly Gly Ala Val Leu
        305                 310                 315
Thr Lys Ala Thr Val Gln Ser Val Leu Leu Asp Ser Ala Gly Lys
        320                 325                 330
Ala Cys Gly Val Ser Val Lys Lys Gly His Glu Leu Val Asn Ile
        335                 340                 345
Tyr Cys Pro Ile Val Val Ser Asn Ala Gly Leu Phe Asn Thr Tyr
        350                 355                 360
Glu His Leu Leu Pro Gly Asn Ala Arg Cys Leu Pro Gly Val Lys
        365                 370                 375
Gln Gln Leu Gly Thr Val Arg Pro Gly Leu Gly Met Thr Ser Val
        380                 385                 390
Phe Ile Cys Leu Arg Gly Thr Lys Glu Asp Leu His Leu Pro Ser
        395                 400                 405
Thr Asn Tyr Tyr Val Tyr Tyr Asp Thr Asp Met Asp Gln Ala Met
        410                 415                 420
Glu Arg Tyr Val Ser Met Pro Arg Glu Glu Ala Ala Glu His Ile
        425                 430                 435
Pro Leu Leu Phe Phe Ala Phe Pro Ser Ala Lys Asp Pro Thr Trp
        440                 445                 450
Glu Asp Arg Phe Pro Gly Arg Ser Thr Met Ile Met Leu Ile Pro
        455                 460                 465
Thr Ala Tyr Glu Trp Phe Glu Glu Trp Gln Ala Glu Leu Lys Gly
        470                 475                 480
Lys Arg Gly Ser Asp Tyr Glu Thr Phe Lys Asn Ser Phe Val Glu
        485                 490                 495
Ala Ser Met Ser Val Val Leu Lys Leu Phe Pro Gln Leu Glu Gly
        500                 505                 510
Lys Val Glu Ser Val Thr Ala Gly Ser Pro Leu Thr Asn Gln Phe
        515                 520                 525
Tyr Leu Ala Ala Pro Arg Gly Ala Cys Tyr Gly Ala Asp His Asp
        530                 535                 540
Leu Gly Arg Leu His Pro Cys Val Met Ala Ser Leu Arg Ala Gln
        545                 550                 555
Ser Pro Ile Pro Asn Leu Tyr Leu Thr Gly Gln Asp Ile Phe Thr
        560                 565                 570
Cys Gly Leu Val Gly Ala Leu Gln Gly Ala Leu Leu Cys Ser Ser
        575                 580                 585
Ala Ile Leu Lys Arg Asn Leu Tyr Ser Asp Leu Lys Asn Leu Asp
        590                 595                 600
Ser Arg Ile Arg Ala Gln Lys Lys Asn
        605                 610

<210> SEQ ID NO 13
<211> LENGTH: 415
<212> TYPE: PRT
<213> ORGANISM: Homo sapiens
```

-continued

```
<220> FEATURE:
<221> NAME/KEY: misc_feature
<223> OTHER INFORMATION: Incyte ID No.: 2906094CD1

<400> SEQUENCE: 13

Met Leu Trp Ser Gly Cys Arg Arg Phe Gly Ala Arg Leu Gly Cys
 1               5                  10                  15

Leu Pro Gly Gly Leu Arg Val Leu Val Gln Thr Gly His Arg Ser
            20                  25                  30

Leu Thr Ser Cys Ile Asp Pro Ser Met Gly Leu Asn Glu Glu Gln
        35                  40                  45

Lys Glu Phe Gln Lys Val Ala Phe Asp Phe Ala Ala Arg Glu Met
    50                  55                  60

Ala Pro Asn Met Ala Glu Trp Asp Gln Lys Glu Leu Phe Pro Val
65                  70                  75

Asp Val Met Arg Lys Ala Ala Gln Leu Gly Phe Gly Gly Val Tyr
            80                  85                  90

Ile Gln Thr Asp Val Gly Gly Ser Gly Leu Ser Arg Leu Asp Thr
        95                 100                 105

Ser Val Ile Phe Glu Ala Leu Ala Thr Gly Cys Thr Ser Thr Thr
   110                 115                 120

Ala Tyr Ile Ser Ile His Asn Met Cys Ala Trp Met Ile Asp Ser
125                 130                 135

Phe Gly Asn Glu Glu Gln Arg His Lys Phe Cys Pro Pro Leu Cys
            140                 145                 150

Thr Met Glu Lys Phe Ala Ser Tyr Cys Leu Thr Glu Pro Gly Ser
        155                 160                 165

Gly Ser Asp Ala Ala Ser Leu Leu Thr Ser Ala Lys Lys Gln Gly
   170                 175                 180

Asp His Tyr Ile Leu Asn Gly Ser Lys Ala Phe Ile Ser Gly Ala
185                 190                 195

Gly Glu Ser Asp Ile Tyr Val Val Met Cys Arg Thr Gly Gly Pro
            200                 205                 210

Gly Pro Lys Gly Ile Ser Cys Ile Val Val Glu Lys Gly Thr Pro
        215                 220                 225

Gly Leu Ser Phe Gly Lys Lys Glu Lys Lys Val Gly Trp Asn Ser
   230                 235                 240

Gln Pro Thr Arg Ala Val Ile Phe Glu Asp Cys Ala Val Pro Val
245                 250                 255

Ala Asn Arg Ile Gly Ser Glu Gly Gln Gly Phe Leu Ile Ala Val
            260                 265                 270

Arg Gly Leu Asn Gly Gly Arg Ile Asn Ile Ala Ser Cys Ser Leu
        275                 280                 285

Gly Ala Ala His Ala Ser Val Ile Leu Thr Arg Asp His Leu Asn
   290                 295                 300

Val Arg Lys Gln Phe Gly Glu Pro Leu Ala Ser Asn Gln Tyr Leu
305                 310                 315

Gln Phe Thr Leu Ala Asp Met Ala Thr Arg Leu Val Ala Ala Arg
            320                 325                 330

Leu Met Val Arg Asn Ala Ala Val Ala Leu Gln Glu Glu Arg Lys
        335                 340                 345

Asp Ala Val Ala Leu Cys Ser Met Ala Lys Leu Phe Ala Thr Asp
   350                 355                 360

Glu Cys Phe Ala Ile Cys Asn Gln Ala Leu Gln Met His Gly Gly
```

```
                         365                 370                 375
Tyr Gly Tyr Leu Lys Asp Tyr Ala Val Gln Gln Tyr Val Arg Asp
            380                 385                 390

Ser Arg Val His Gln Ile Leu Glu Gly Ser Asn Glu Val Met Arg
            395                 400                 405

Ile Leu Ile Ser Arg Ser Leu Leu Gln Glu
            410                 415

<210> SEQ ID NO 14
<211> LENGTH: 274
<212> TYPE: PRT
<213> ORGANISM: Homo sapiens
<220> FEATURE:
<221> NAME/KEY: misc_feature
<223> OTHER INFORMATION: Incyte ID No.: 3294314CD1

SEQUENCE: 14

Met Ala Ala Ala Glu Pro Ser Pro Arg Arg Val Gly Phe Val Gly
  1               5                  10                  15

Ala Gly Arg Met Ala Gly Ala Ile Ala Gln Gly Leu Ile Arg Ala
             20                  25                  30

Gly Lys Val Glu Ala Gln His Ile Leu Ala Ser Ala Pro Thr Asp
             35                  40                  45

Arg Asn Leu Cys His Phe Gln Ala Leu Gly Cys Arg Thr Thr His
             50                  55                  60

Ser Asn Gln Glu Val Leu Gln Ser Cys Leu Leu Val Ile Phe Ala
             65                  70                  75

Thr Lys Pro His Val Leu Pro Ala Val Leu Ala Glu Val Ala Pro
             80                  85                  90

Val Val Thr Thr Glu His Ile Leu Val Ser Val Ala Ala Gly Val
             95                 100                 105

Ser Leu Ser Thr Leu Glu Glu Leu Leu Pro Pro Asn Thr Arg Val
            110                 115                 120

Leu Arg Val Leu Pro Asn Leu Pro Cys Val Val Gln Glu Gly Ala
            125                 130                 135

Ile Val Met Ala Arg Gly Arg His Val Gly Ser Ser Glu Thr Lys
            140                 145                 150

Leu Leu Gln His Leu Leu Glu Ala Cys Gly Arg Cys Glu Glu Val
            155                 160                 165

Pro Glu Ala Tyr Val Asp Ile His Thr Gly Leu Ser Gly Ser Gly
            170                 175                 180

Val Ala Phe Val Cys Ala Phe Ser Glu Ala Leu Ala Glu Gly Ala
            185                 190                 195

Val Lys Met Gly Met Pro Ser Ser Leu Ala His Arg Ile Ala Ala
            200                 205                 210

Gln Thr Leu Leu Gly Thr Ala Lys Met Leu His Glu Gly Gln
            215                 220                 225

His Pro Ala Gln Leu Arg Ser Asp Val Cys Thr Pro Gly Gly Thr
            230                 235                 240

Thr Ile Tyr Gly Leu His Ala Leu Glu Gln Gly Gly Leu Arg Ala
            245                 250                 255

Ala Thr Met Ser Ala Val Glu Ala Ala Thr Cys Arg Ala Lys Glu
            260                 265                 270

Leu Ser Arg Lys
```

```
<210> SEQ ID NO 15
<211> LENGTH: 283
<212> TYPE: PRT
<213> ORGANISM: Homo sapiens
<220> FEATURE:
<221> NAME/KEY: misc_feature
<223> OTHER INFORMATION: Incyte ID No.: 4940951CD1

<400> SEQUENCE: 15

Met Ala Ala Pro Phe Phe Ser Thr Pro Phe Gln Pro Tyr Val Tyr
  1               5                  10                  15

Gln Ser Gln Gln Gly Ser Val Thr Ala Phe Gln Ile Ser Gly Gly
                 20                  25                  30

Asp Val Gln Val Leu Gln Val Met Leu Lys Ser Gln Glu Lys Leu
                 35                  40                  45

Thr Ala Lys Pro Gly Ala Met Cys Tyr Met Ser Gly Asn Met Gln
                 50                  55                  60

Met Asp Asn Asn Tyr Leu Pro Glu Asn Asp Gly Gly Val Trp Gln
 65                  70                  75

Trp Ile Phe Gly Lys Arg Val Ser Ser Thr Ile Phe Phe Asn Ser
                 80                  85                  90

Gly Ser Asp Asp Gly Tyr Val Gly Ile Ala Ala Pro Phe Pro Gly
                 95                 100                 105

Arg Ile Leu Pro Val Asp Leu Thr Asn Phe Ser Gly Glu Leu Leu
                110                 115                 120

Cys Gln Ala Asp Ala Phe Leu Cys Ser Val Asn Asp Val Ser Val
                125                 130                 135

Ser Ser Thr Val Glu Pro Arg Pro Arg Asn Ile Glu Ile Gly Ala
                140                 145                 150

Glu Met Ile Leu Lys Gln Lys Leu Arg Gly Gln Gly Met Ala Phe
                155                 160                 165

Leu Val Gly Gly Gly Ser Val Met Gln Lys Ile Leu Ala Pro Arg
                170                 175                 180

Glu Val Ile Thr Val Asp Ala Ala Cys Ile Val Ala Met Ser Ala
                185                 190                 195

Thr Ile Asn Phe Gln Leu Lys Ser Pro Asn Gln Leu Arg Arg Ala
                200                 205                 210

Val Phe Gly Gly Asp Asn Gln Leu Thr Ala Ser Leu Thr Gly Pro
                215                 220                 225

Gly Val Val Phe Ile Gln Ser Leu Pro Phe His Arg Leu Ser Gln
                230                 235                 240

Arg Ile Ala Ser Ser Arg Ser Val Ala Gly Pro Ser Leu Arg Asp
                245                 250                 255

Asn Pro Lys Phe Phe Ile Gln Ile Val Met Phe Phe Phe Leu Ala
                260                 265                 270

Tyr Val Met Ile Val Ser Ser Ile Ile Leu Thr Asp Val
                275                 280

<210> SEQ ID NO 16
<211> LENGTH: 2471
<212> TYPE: DNA
<213> ORGANISM: Homo sapiens
<220> FEATURE:
<221> NAME/KEY: misc_feature
<223> OTHER INFORMATION: Incyte ID No.: 000746CB1

<400> SEQUENCE: 16
gcgctcctcg cagcaccgta gtgcgcttgc gctgagcagc ccgcgagggc ggaagtggga      60
```

-continued

| | |
|---|---|
| gctgcgaccg cgctccctgt gaggtgggca agcggcgaaa tggcgccctc cgggagtctt | 120 |
| gcagttcccc tggcagtcct ggtgctgttg ctttggggtg ctccctggac gcacgggcgg | 180 |
| cggagcaacg ttcgcgtcat cacggacgag aactggagaa aactgctgga aggagactgg | 240 |
| atgatagaat tttatgcccc gtggtgccct gcttgtcaaa atcttcaacc ggaatgggaa | 300 |
| agttttgctg aatggggaga agatcttgag gttaatattg cgaaagtaga tgtcacagag | 360 |
| cagccaggac tgagtggacg gtttatcata actgctcttc ctactattta tcattgtaaa | 420 |
| gatggtgaat ttaggcgcta tcagggtcca aggactaaga aggacttcat aaactttata | 480 |
| agtgataaag agtggaagag tattgagccc gtttcatcat ggtttggtcc aggttctgtt | 540 |
| ctgatgagta gtatgtcagc actctttcag ctatctatgt ggatcaggac gtgccataac | 600 |
| tactttattg aagaccttgg attgccagtg tggggatcat atactgtttt tgctttagca | 660 |
| actctgtttt ccggactgtt attaggactc tgtatgatat ttgtggcaga ttgcctttgt | 720 |
| ccttcaaaaa ggcgcagacc acagccatac ccatacccett caaaaaaatt attatcagaa | 780 |
| tctgcacaac ctttgaaaaa agtggaggag gaacaagagg cggatgaaga agatgtttca | 840 |
| gaagaagaag ctgaaagtaa agaaggaaca aacaaagact tcccacagaa tgccataaga | 900 |
| caacgctctc tgggtccatc attggccaca gataaatcct agttaaattt tatagttatc | 960 |
| ttaatattat gattttgata aaaacagaag attgatcatt ttgtttggtt tgaagtgaac | 1020 |
| tgtgactttt ttgaatattg cagggttcag tctagattgt cattaaattg aagagtctac | 1080 |
| attcagaaca taaaagcact aggtatacaa gtttgaaata tgatttaagc acagtatgat | 1140 |
| ggtttaaata gttctctaat ttttgaaaaa tcgtgccaag caataagatt tatgtatatt | 1200 |
| tgtttaataa taacctattt caagtctgag ttttgaaaat ttacatttcc caagtattgc | 1260 |
| attattgagg tatttaagaa gattatttta gagaaaaata tttctcattt gatataattt | 1320 |
| ttctctgttt cactgtgtga aaaaagaag atatttccca taaatgggaa gtttgcccat | 1380 |
| tgtctcaaga aatgtgtatt tcagtgacaa tttcgtggtc ttttagagg tatattccaa | 1440 |
| aatttccttg tatttttagg ttatgcaact aataaaaact accttacatt aattaattac | 1500 |
| agttttctac acatggtaat acaggatatg ctactgattt aggaagtttt taagttcatg | 1560 |
| gtattctctt gattccaaca aagtttgatt ttctctgtgta ttttcttac ttactatggg | 1620 |
| ttacattttt tatttttcaa attggatgat aatttcttgg aaacattttt tatgttttag | 1680 |
| taaacagtat ttttttgttg tttcaaactg aagtttactg agagatccat caaattgaac | 1740 |
| aatctgttgt aatttaaaat tttggccact ttttttcagat tttacatcat tcttgctgaa | 1800 |
| cttcaacttg aaattgtttt tttttctttt ttggatgtga aggtgaacat tcctgatttt | 1860 |
| tgtctgatgt gaaaaagcct tggtatttta catttgaaaa attcaaagaa gcttaatata | 1920 |
| aaagtttgca ttctactcag gaaaaagcat cttcttgtat atgtcttaaa tgtattttg | 1980 |
| tcctcatata cagaaagttc ttaattgatt ttacagtctg taatgcttga tgttttaaaa | 2040 |
| taataacatt tttatatttt ttaaaagaca aacttcatat tatcctgtgt tctttcctga | 2100 |
| ctggtaatat tgtgtgggat ttcacaggta aaagtcagta ggatggaaca ttttagtgta | 2160 |
| tttttactcc ttaaagagct agaatacata gttttcacct taaagaagg gggaaaatca | 2220 |
| taaatacaat gaatcaactg accattacgt agtagacaat ttctgtaatg tccccttctt | 2280 |
| tctaggctct gttgctgtgt gaatccatta gatttacagt atcgtaatat acaagttttc | 2340 |
| tttaaagccc tctccttag aatttaaaat attgtaccat tgaagagttt ggatgtgtaa | 2400 |

| | |
|---|---:|
| cttgtgatgc cttagaaaaa tatcctaagc acaaaataaa cctttctaac cacttcatta | 2460 |
| aaaaaaaaaa a | 2471 |

<210> SEQ ID NO 17
<211> LENGTH: 822
<212> TYPE: DNA
<213> ORGANISM: Homo sapiens
<220> FEATURE:
<221> NAME/KEY: misc_feature
<223> OTHER INFORMATION: Incyte ID No.: 2472577CB1

<400> SEQUENCE: 17

| | |
|---|---:|
| cggacccagc gccgcccgcg cgaactccct ggtgttgtgc gcccttcccc gcgcgcggcc | 60 |
| cctcctgctg ggctggggtc tgtggctgac gtccgctttt cccggaacgg caaagagaag | 120 |
| tcattcagaa ttcaaaagaa gttctaagtt tattgcaaga aaaaaccct gccttcaagc | 180 |
| cggttcttgc aattatccag gcaggtacga caacttgat gcaggaaatc aaccagaatt | 240 |
| tggctgagga ggctggtctg aacatcactc acatttgcct ccctccagat agcagtgaag | 300 |
| ccgagattat agatgaaatc ttaaagatca atgaagatac cagagtacat ggccttgccc | 360 |
| ttcagatctc tgagaacttg tttagcaaca aagtcctcaa tgccttgaaa ccagaaaaag | 420 |
| atgtggatgg agtaacagac ataaacctgg ggaagctggt gcgaggggat gcccatgaat | 480 |
| gttttgtttc acctgttgcc aaagctgtaa ttgaacttct tgaaaaatca gtaggtgtca | 540 |
| acctagatgg aaagaagatt ttggtagtgg gggcccatgg gtctttggaa gctgctctac | 600 |
| aatgcctgtt ccagagaaaa gggtccatga caatgagcat ccagtggaaa acacgccagc | 660 |
| ttcaaagcaa gacggagtct cgttctgtca ccaggctgga gtgcaggcgc gtgatctagg | 720 |
| ctcactgcaa gctctgcctc ccaggttgaa gtgattctcc tgtgaaaggg aattattttt | 780 |
| gatgagtcat taaagtatat ccattcccag aaaaaaaaa aa | 822 |

<210> SEQ ID NO 18
<211> LENGTH: 2026
<212> TYPE: DNA
<213> ORGANISM: Homo sapiens
<220> FEATURE:
<221> NAME/KEY: misc_feature
<223> OTHER INFORMATION: Incyte ID No.: 2160405CB1

<400> SEQUENCE: 18

| | |
|---|---:|
| aggaagccgg ccacacccct tttggactcg catggggcac tgtccaatat tctttcatca | 60 |
| gggcgtgggg tctgtccaat gttcgtaggg gccgtctccc ggtgggggac cagttaaacc | 120 |
| agcgggattt agtatggcgg attcacagga tgagccacga tgcattgctt cacatggacc | 180 |
| aagccagcaa acaacttgga aagccatgag acaagaagtg gaactgctta agatcactcg | 240 |
| atcatcaatg atggaatcta actgagcaaa aatcttcttc ttcagttcta gatcttctgg | 300 |
| aacacattcc tgaatgtgca tggcgccctc tactgcttct tggatattgg gacaaccact | 360 |
| gatgagtgac agctgctctt ccacactcag ggagcctttc agagaacctg cctgctccag | 420 |
| caacttcatc tcctttctga tgttttccag ggcgttcctt atctgctgtt gctcaatgtc | 480 |
| atagagtttc acctggaagc ctccactggc aaacagcgtg gcccgagttc gcccaatgac | 540 |
| tccactgcca acgatcacca cgcagccgcc cgcggcgccg cgtccccggc caaccatgg | 600 |
| cgtcctccgc ggccggctgc gtggtgatcg ttggcagtgg agtcattggg cgaagctggg | 660 |
| ccatgctgtt tgccagtgga ggcttccagg tgaaactcta tgacattgag caacagcaga | 720 |
| taaggaacgc cctggaaaac atcagaaagg agatgaagtt gctggagcag gcaggttctc | 780 |

-continued

```
tgaaaggctc cctgagtgtg aagagcagc tgtcactcat cagtggttgt cccaatatcc      840
aagaagcagt agaggcgcc atgcacattc aggaatgtgt tccagaagat ctagaactga      900
agaagaagat ttttgctcag ttagattcca tcattgatga tcgagtgatc ttaagcagtt     960
ccacttcttg tctcatgcct tccaagttgt ttgctggctt ggtccatgtg aagcaatgca    1020
tcgtggctca tcctgtgaat ccgccatact acatcccgct ggttgagctg gtccccccacc   1080 cggagacggc ccctacgaca gtggacagaa cccacgccct gatgaagaag attggacagt   1140
gccccatgcg agtccagaag gaggtggccg gcttcgttct gaaccgcctg caatatgcaa    1200
tcatcagcga ggcctggcgg ctagtggagg aaggaatcgt gtctcctagt gacctggacc    1260
ttgtcatgtc agaagggttg ggcatgcggt atgcattcat tggaccccctg gaaaccatgc    1320 atctcaatgc agaaggtatg ttaagctact gcgacagata cagcgaaggc ataaaacatg    1380
tcctacagac ttttggaccc attccagagt tttccaggc cactgctgag aaggttaacc    1440
aggacatgtg catgaaggtc cctgatgacc cggagcactt agctgccagg aggcagtgga    1500
gggacgagtg cctcatgaga ctcgccaagt tgaagagtca agtgcagccc cagtgaattt    1560
cttgtaatgc agcttccact cctctcattg gaggccctat ttgggaacac tgcaagccct    1620
taatcagccc tctgtgacat aggtagcagc ccacggagat cctaagctgg ctgtcttgtg    1680
tgcagcctga gtgggtggt gcaggccggt agtctgcccg tcactttgga tcatagccct     1740
gggcctggcg gcacagcagc acttgcgttc tcggggctgt cgatttcctg ccacctgggc    1800
agataacctg gagattttca ccttttcttt tcagcttgat gcatttgac tatatttttac    1860 agccagtgat tgtagtttca tgttaatatg tggcaaaata tttttgtaat tattttctaa    1920
tcccttcctg agtactctgg ggccctgcat ttatgaggca cctaccttca ttttgctaac    1980
gcttattctg aataaaagtt tttgattcct taaaaaaaaa aaaaaa                    2026
```

<210> SEQ ID NO 19
<211> LENGTH: 1243
<212> TYPE: DNA
<213> ORGANISM: Homo sapiens
<220> FEATURE:
<221> NAME/KEY: misc_feature
<223> OTHER INFORMATION: Incyte ID No.: 2591695CB1

<400> SEQUENCE: 19

```
tccgcgggct agcgggcggt gggggcgcca cagcgcggaa ggcgggcacg cgggccatgg      60
ctccctgggc ggaggccgag cactcggcgc tgaacccgct gcgcgcggtg tggctcacgc     120
tgaccgccgc cttcctgctg accctactgc tgcagctcct gccgcccggc ctgctcccgg     180
gctgcgcgat cttccaggac ctgatccgct atgggaaaac caagtgtggg gagccgtcgc     240
gccccgccgc ctgccgagcc tttgatgtcc ccaagagata tttttcccac tttatatca     300 tctcagtgct gtgaatggc ttcctgcttt ggtgccttac tcaatctctg ttcctgggag     360
caccttttcc aagctggctt catggtttgc tcagaattct cggggcggca cagttccagg    420
gaggggagct ggcactgtct gcattcttag tgctagtatt tctgtggctg cacagcttac    480
gaagactctt cgagtgcctc tacgtcagtg tcttctccaa tgtcatgatt cacgtcgtgc    540
agtactgttt tggacttgtc tattatgtcc ttgttggcct aactgtgctg agccaagtgc    600
caatggatgg caggaatgcc tacataacag ggaaaaatct attgatgcaa gcacggtggt    660
tccatattct tgggatgatg atgttcatct ggtcatctgc ccatcagtat aagtgccatg    720
ttattctcgg caatctcagg aaaaataaag caggagtggt cattcactgt aaccacagga    780
```

-continued

```
tcccatttgg agactggttt gaatatgttt cttcccctaa ctacttagca gagctgatga    840
tctacgtttc catggccgtc acctttgggt tccacaactt aacttggtgg ctagtggtga    900
caaatgtctt ctttaatcag gccctgtctg cctttctcag ccaccaattc tacaaaagca    960
aatttgtctc ttacccgaag cataggaaag ctttcctacc attttgtttt taagttaacc   1020
tcagtcatga agaatgcaaa ccaggtgatg gtttcaatgc ctaaggacag tgaagtctgg   1080
agcccaaagt acagtttcag caaagctgtt tgaaactctc cattccattt ctataccccca  1140 caagttttca ctgaatgagc atggcagtgc cactcaagaa aatgaatctc caaagtatct   1200
tcaaagaata aatactaatg gcagatctgc gaaaaaaaaa aaa                     1243

<210> SEQ ID NO 20
<211> LENGTH: 1921
<212> TYPE: DNA
<213> ORGANISM: Homo sapiens
<220> FEATURE:
<221> NAME/KEY: misc_feature
<223> OTHER INFORMATION: Incyte ID No.: 474100CB1

<400> SEQUENCE: 20
gtgaagctgc tcctcacgtt ttggcgtgcc tgcgctctct gcaggcagaa gcgaacaaag     60
acccagcaag agaaggcaga ggctaagacc catcccgtat ctgctctcct gaaataattc    120
tggagtcatg cctgaaatgc cagaggacat ggagcaggag gaagttaaca tccctaatag    180
gagggttctg gttactggtg ccactgggct tcttggcaga gctgtacaca aagaatttca    240
gcagaataat tggcatgcag ttggctgtgg tttcagaaga gcaagaccaa aatttgaaca    300
ggttaatctg ttggattcta atgcagttca tcacatcatt catgattttc agccccatgt    360
tatagtacat tgtgcagcag agagaagacc agatgttgta gaaaatcagc cagatgctgc    420
ctctcaactt aatgtggatg cttctgggaa tttagcaaag gaagcagatt ttttttttt    480 ttttgtagct gctgttggag catttctcat ctacattagc tcagattatg tatttgatgg    540
aacaaatcca ccttacagag aggaagacat accagctccc ctaaatttgt atggcaaaac    600
aaaattagat ggagaaaagg ctgtcctgga gaacaatcta ggagctgctg ttttgaggat    660
tcctattctg tatggggaag ttgaaaagct cgaagaaagt gctgtgactg ttatgtttga    720
taaagtgcgg ttcagcaaca agtcagcaaa catggatcac tggcagcaga ggttccccac    780
acatgtcaaa gatgtggcca ctgtgtgccg gcagctagca gagaagagaa tgctggatcc    840
atcaattaag ggaacctttc actggtctgg caatgaacag atgactaagt atgaaatggc    900
atgtgcaatt gcagatgcct tcaacctccc cagcagtcac ttaagaccta ttactgacag    960
ccctgtccta ggagcacaac gtccgagaaa tgctcagctt gactgctcca aattggagac   1020
cttgggcatt ggccaacgaa caccatttcg aattggaatc aaagaatcac tttggccttt   1080
cctcattgac aagagatgga gacaaacggt ctttcattag tttatttgtg ttgggttctt   1140 ttttttttt aaatgaaaag tatagtatgt ggcactttt aaagaacaaa ggaaatagtt    1200
ttgtatgagt actttaattg tgactcttag gatctttcag gtaaatgatg ctcttgcact   1260
agtgaaattg tctaaagaaa ctaaagggca gtcatgccct gtttgcagta atttttcttt   1320 ttatcattt gtttgtcctg gctaaacttg gagtttgagt atagtaaatt atgatcctta    1380
aatatttgag agtcaggatg aagcagatct gctgtagact tttcagatga aattgttcat   1440
tctcgtaacc tccatatttt caggatttt gaagctgttg accttttcat gttgattatt    1500
ttaaattgtg tgaaatagta taaaaatcat tggtgttcat tatttgcttt gcctgagctc    1560
```

```
agatcaaaat gtttgaagaa aggaacttta tttttgcaag ttacgtacag tttttatgct    1620
tgagatattt caacatgtta tgtatattgg aacttctaca gcttgatgcc tcctgctttt    1680
atagcagttt atggggagca cttgaaagag cgtgtgtaca tgtattttt ttctaggcaa     1740 acattgaatg caaacgtgta ttttttaat ataaatatat aactgtcctt ttcatcccat     1800
gttgccgcta agtgatattt catatgtgtg gttatactca taataatggg ccttgtaagt    1860
cttttcacca ttcatgaata taataaaata tgtactgctg gcatgtaaaa aaaaaaaaa     1920 a                                                                    1921
```

<210> SEQ ID NO 21
<211> LENGTH: 1261
<212> TYPE: DNA
<213> ORGANISM: Homo sapiens
<220> FEATURE:
<221> NAME/KEY: misc_feature
<223> OTHER INFORMATION: Incyte ID No.: 1304767CB1

<400> SEQUENCE: 21

```
ggggcctgga ctcccgagtc tgagggagga gggactgagg cttctggatt cctgggtctg    60
tgggaggagg gactggggct cctggattcc tgggtctgtg ggaagagagg agtgtctgag    120
ggaggagggg ctgggacaa  acttccaggt ctctagcctt cctggcaacg ccccccgagg    180
ccggacttcc aggatccagc ctctattgag gatttgatgc gacggcctca cggggctttg    240
gaggtgaaag aggcccagag tagagagaga gagagaccga cgtacacggg atggctacgg    300
gaacgcgcta tgccgggaag gtggtggtcg tgaccggcat cggagctggg atcgtgcgcg    360
ccttcgtgga cagcggggcc cgagtggtta tctgcgacaa ggatgagtct gggggccggg    420
ccctggagca ggagctccct ggagctgtct ttatcctctg tgatgtgact caggaagatg    480
atgtgaagac cctggtttct gagaccatcc gccgatttgg ccgcctggat tgtgttgtca    540
acaacgctgg ccaccaccca cccccacaga ggcctgagga gacctctgcc cagggattcc    600
gccagctgct ggagctgaac ctactgggga cgtacacctt gaccaagctc gccctcccct    660
acctgcggaa gagtcaaggg aatgtcatca acatctccag cctggtgggg gcaatcggcc    720
aggcccaggc agttccctat gtggccacca agggggcagt aacagccatg accaaagctt    780
tggccctgga tgaaagtcca tatggtgtcc gagtcaactg tatctcccca ggaaacatct    840 ggacccccgct gtgggaggag ctggcagcct aatgccaga ccctaggggcc acaatccgag    900 agggcatgct ggcccagcca ctgggccgca tgggccagcc cgctgaggtc ggggctgcgg    960
cagtgttcct ggcctccgaa gccaacttct gcacgggcat tgaactgctc gtgacggggg    1020
gtgcagagct ggggtacggg tgcaaggcca gtcggagcac cccgtggac gcccccgata     1080 tcccttcctg atttctctca tttctacttg ggccccctt cctaggactc tcccacccca    1140
aactccaacc tgtatcagat gcagcccca agcccttaga ctctaagccc agttagcaag    1200
gtgccgggtc accctgcagg ttcccataaa aacgatttgc agccagaaaa aaaaaaaaa   1260 a                                                                    1261
```

<210> SEQ ID NO 22
<211> LENGTH: 1801
<212> TYPE: DNA
<213> ORGANISM: Homo sapiens
<220> FEATURE:
<221> NAME/KEY: misc_feature
<223> OTHER INFORMATION: Incyte ID No.: 1465978CB1

```
<400> SEQUENCE: 22 cagcttttt  tttttttttt  tttttttttt  taatcttgca  ctttgaaacc  gcgggaccga    60
ggcagggtgc  gcgcgtgtgg  ttggtgcctt  tttttttttt  tcttcccctc  cctaaactcc   120
tctgtcagtc  tgtaaacatt  acctgagaat  tccccagccg  aaacggctgc  tggggcaaga   180
aacttcttgt  tagaactttc  cacctccggc  ttcccctcc   acctctttta  ccgtcccaac   240
cttaggagac  gcttttctc   ccccagagga  gaatttatct  tttttttttt  tttttttttc   300
tttttctcac  ccggtgcttt  gcatttggga  agaggtgatt  tcaagagtgg  ccaggtggga   360
cgcctctctc  ctccttattc  ggtttactat  ttattgttcg  gggtgttttt  taattcctgt   420
attgctcggc  ccggggagtt  tcgcccctg   cccggctccg  cggcgcggag  gatggtgtgg   480
aaacggctgg  gcgcgctggt  gatgttccct  ctacagatga  tctatctggt  ggtgaaagca   540
gccgtcggac  tggtgctgcc  cgccaagctg  cgggacctgt  cgcgggagaa  cgtcctcatc   600
accggcggcg  ggagaggcat  cgggcgtcag  ctcgcccgcg  agttcgcgga  gcgcggcgcc   660
agaaagattg  ttctctgggg  ccggactgag  aaatgcctga  aggagacgac  ggaggagatc   720
cggcagatgg  gcactgagtg  ccattacttc  atctgtgatg  tgggcaaccg  ggaggaggtg   780
taccagacgg  ccaaggccgt  ccgggagaag  gtgggtgaca  tcaccatcct  ggtgaacaat   840
gccgccgtgg  tccatgggaa  gagcctaatg  gacagtgatg  atgatgccct  cctcaagtcc   900
caacacatca  acaccctggg  ccagttctgg  accaccaagg  ccttcctgcc  acgtatgctg   960
gagctgcaga  atggccacat  cgtgtgcctc  aactccgtgc  tggcactgtc  tgccatcccc  1020
ggtgccatcg  actactgcac  atccaaagcg  tcagccttcg  ccttcatgga  gagcctgacc  1080
ctggggctgc  tggactgtcc  gggagtcagc  gccaccacag  tgctgccctt  ccacaccagc  1140
accgagatgt  tccagggcat  gagagtcagg  tttcccaacc  tctttccccc  actgaagccg  1200
gagacggtgg  cccggaggac  agtggaagct  gtgcagctca  accaggccct  cctcctcctc  1260
ccatggacaa  tgcatgccct  cgttatcttg  aaaagcatac  ttccacaggc  tgcactcgag  1320
gagatccaca  aattctcagg  aacctacacc  tgcatgaaca  cttcaaagg   gcggacatag  1380
agacaggatg  aagacatgct  tgaggagcca  cggagtttgg  gggccacagc  acctgggcac  1440
acacccgagc  acctgtccat  tggcatgctt  ctgctgggtg  agcaggacag  ctcctgtccc  1500
cagcgaagaa  tccggctgcc  cctgggccag  tcccaggacc  tttgcacagg  actgatgggt  1560
gtaactgacc  cccacaggga  ggcaggaaaa  cagccagaag  ccaccttgac  acttttgaac  1620
atttccagtt  ctgtagagtt  tattgtcaat  tgcttctcaa  gtctaaccag  cctcagcagt  1680
gtgcatagac  catttccagg  agggtctgtc  cccagatgct  ctgcctcccg  ttccaaaacc  1740
cactcatcct  cagcttgcac  aaactggttg  aacggcagga  atgaaaaata  aagacgagat  1800
a                                                                       1801

<210> SEQ ID NO 23
<211> LENGTH: 1711
<212> TYPE: DNA
<213> ORGANISM: Homo sapiens
<220> FEATURE:
<221> NAME/KEY: misc_feature
<223> OTHER INFORMATION: Incyte ID No.: 1635966CB1

<400> SEQUENCE: 23
tttgatacgg  gagttcctcc  ttgctctcgc  ccctactctt  tctggtgtta  gatcgagcta    60
ccctctaaaa  gcagtttaga  gtggtaaaaa  aaaaaaaaaa  acacaccaaa  cgctcgcagc   120
```

-continued

| | |
|---|---|
| cacaaaaggg atgaaatttc ttctggacat cctcctgctt ctcccgttac tgatcgtctg | 180 |
| ctccctagag tccttcgtga agcttttat tcctaagagg agaaaatcag tcaccggcga | 240 |
| aatcgtgctg attacaggag ctgggcatgg aattgtgaga ctgactgcct atgaatttgc | 300 |
| taaacttaaa agcaagctgg ttctctggga tataaataag catggactgg aggaaacagc | 360 |
| tgccaaatgc aagggactgg gtgccaaggt tcatacctttt gtggtagact gcagcaaccg | 420 |
| agaagatatt tacagctctg caaagaaggt gaaggcagaa attggagatg ttagtatttt | 480 |
| agtaaataat gctggtgtag tctatacatc agatttgttt gctacacaag atcctcagat | 540 |
| tgaaaagact tttgaagtta atgtacttgc acatttctgg actacaaagg catttcttcc | 600 |
| tgcaatgacg aagaataacc atggccatat tgtcactgtg gcttcggcag ctggacatgt | 660 |
| ctcggtcccc ttcttactgg cttactgttc aagcaagttt gctgctgttg gatttcataa | 720 |
| aactttgaca gatgaactgg ctgccttaca ataactgga gtcaaaacaa catgtctgtg | 780 |
| tcctaatttc gtaaacactg gcttcatcaa aaatccaagt acaagtttgg gacccactct | 840 |
| ggaacctgag gaagtggtaa acaggctgat gcatgggatt ctgactgagc agaagatgat | 900 |
| ttttattcca tcttctatag ctttttttaac aacattggaa aggatccttc ctgagcgttt | 960 |
| cctggcagtt ttaaaacgaa aaatcagtgt taagtttgat gcagttattg gatataaaat | 1020 |
| gaaagcgcaa taagcaccta gttttctgaa aactgattta ccaggtttag ttgatgtcca | 1080 |
| tctaatagtg ccagaatttt aatgtttgaa cttctgtttt ttctaattat ccccatttct | 1140 |
| tcaatatcat ttttgaggct ttggcagtct tcatttacta ccacttgttc tttagccaaa | 1200 |
| agctgattac atatgatata aacagagaaa tacctttaga ggtgacttta aggaaaatga | 1260 |
| agaaaaagaa ccaaaatgac tttattaaaa taatttccaa gattatttgt ggctcacctg | 1320 |
| aaggctttgc aaaatttgta ccataaccgt ttatttaaca tatatttttta tttttgattg | 1380 |
| cacttaaatt ttgtataatt tgtgtttctt tttctgttct acataaaatc agaaacttca | 1440 |
| agctctctaa ataaaatgaa ggactatatc tagtggtatt tcacaatgaa tatcatgaac | 1500 |
| tctcaatggg taggtttcat cctacccatt gccactctgt ttcctgagag atacctcaca | 1560 |
| ttccaatgcc aaacatttct gcacagggaa gctagaggtg gatacacgtg ttgcaagtat | 1620 |
| aaaagcatca ctgggattta aggagaattg agagaatgta cccacaaatg gcagcaataa | 1680 |
| taaatggatc acacttaaaa aaaaaaaaaa a | 1711 |

<210> SEQ ID NO 24
<211> LENGTH: 2222
<212> TYPE: DNA
<213> ORGANISM: Homo sapiens
<220> FEATURE:
<221> NAME/KEY: misc_feature
<223> OTHER INFORMATION: Incyte ID No.: 1638410CB1

<400> SEQUENCE: 24

| | |
|---|---|
| cttccccggc tctagcaggc cggcttctct gtccaatgcc cacccggagc tgggaggagg | 60 |
| agtctgcgta atgtgcgtgt gaagagactg ggggagctgg ccggggctca cggtgtttga | 120 |
| cccgtcggtc gtgcgtgaga ggaaagggaa ggaggaggtc ccgaatagcg gtcgccgaaa | 180 |
| tgttccggtg tggaggcctg gcggcggggt ctttgaagca gaagctggtg cccttggtgc | 240 |
| ggaccgtgtg cgtccgaagc ccgaggcaga ggaaccggct cccaggcaac ttgttccagc | 300 |
| gatggcatgt tcctctagaa ctccagatga caagacaaat ggctagctct ggtgcatcag | 360 |
| ggggcaaaat cgataattct gtgttagtcc ttattgtggg cttatcaaca gtaggagctg | 420 |

```
gtgcctatgc ctacaagact atgaaagagg acgaaaaaag atacaatgaa agaatttcag      480
ggttagggct gacaccagaa cagaaacaga aaaaggccgc gttatctgct tcagaaggag      540
aggaagttcc tcaagacaag gcgccaagtc atgttccttt cctgctaatt ggtggaggca      600
cagctgcttt tgctgcagcc agatccatcc gggctcggga tcctgggcc agggtactga       660 ttgtatctga agatcctgag ctgccgtaca tgcgacctcc tctttcaaaa gaactgtggt      720
tttcagatga cccaaatgtc acaaagacac tgcgattcaa acagtggaat ggaaaagaga      780
gaagcatata tttccagcca ccttcttct atgtctctgc tcaggacctg cctcatattg       840
agaatggtgg tgtggctgtc ctcactggga agaaggtagt acagctggat gtgagagaca     900
acatggtgaa acttaatgat ggctctcaaa taacctatga aaagtgcttg attgcaacag      960
gaggtactcc aagaagtctg tctgccattg atagggctgg agcagaggtg aagagtagaa     1020
caacgctttt cagaaagatt ggagacttta aagcttgga aagatttca cgggaagtca       1080 aatcaattac gattatcggt gggggcttcc ttggtagcga actggcctgt gctcttggca     1140
gaaaggctcg agccttgggc acagaagtga ttcaactctt ccccgagaaa ggaaatatgg     1200
gaaagatcct ccccgaatac ctcagcaact ggaccatgaa aaaagtcaga cgagagggg     1260 ttaaggtgat gcccaatgct attgtgcaat ccgttggagt cagcagtggc aagttactta     1320
tcaagctgaa agacggcagg aaggtagaaa ctgaccacat agtggcagct gtgggcctgg     1380
agcccaatgt tgagttggcc aagactggtg gcctggaaat agactcagat tttggtggct     1440
tccgggtaaa tgcagagcta caagcacgct ctaacatctg ggtggcagga gatgctgcat     1500
gcttctacga tataaagttg ggaaggaggc gggtagagca ccatgatcac gctgttgtga     1560
gtggaagatt ggctggagaa aatatgactg gagctgctaa gccgtactgg catcagtcaa     1620
tgttctggag tgatttgggc cccgatgttg ctatgaagc tattggtctt gtggacagta     1680
gtttgcccac agttggtgtt tttgcaaaag caactgcaca agacaacccc aaatctgcca     1740
cagagcagtc aggaactggt atccgatcag agagtgagac agagtccgag gcctcagaaa     1800
ttactattcc tcccagcacc ccggcagttc cacaggctcc cgtccagggg gaggactacg     1860
gcaaaggtgt catcttctac ctcagggaca aagtggtcgt ggggattgtg ctatggaaca     1920 tcttaaccg aatgccaata gcaaggaaga tcattaagga cggtgagcag catgaagatc     1980
tcaatgaagt agccaaacta ttcaacattc atgaagactg aagccccaca gtggaattgg     2040
caaacccact gcagcccctg agaggaggtc gaatgggtaa aggagcattt ttttattcag     2100
cagactttct ctgtgtatga gtgtgaatga tcaagtcctt tgtgaatatt ttcaactatg     2160
taggtaaatt cttaatgttc acatagtgaa ataaattctg attcttctaa attaaaaaaa     2220
aa                                                                    2222
```

<210> SEQ ID NO 25
<211> LENGTH: 1278
<212> TYPE: DNA
<213> ORGANISM: Homo sapiens
<220> FEATURE:
<221> NAME/KEY: misc_feature
<223> OTHER INFORMATION: Incyte ID No.: 1743409CB1

<400> SEQUENCE: 25

```
gaggatgaag ttgattgact atggtctctc cggctaccag gaagagtctg ccgaaggtga       60
aggccatgga cttcatcacc tccacagcca tcctgcccct gctgttcggc tgcctgggcg      120
tcttcggcct cttccggctg ctgcagtggg tgcgcgggaa ggcctacctg cggaatgctg      180
```

-continued

| | |
|---|---|
| tggtggtgat cacaggcgcc acctcagggc tgggcaaaga atgtgcaaaa gtcttctatg | 240 |
| ctgcgggtgc taaactggtg ctctgtggcc ggaatggtgg ggccctagaa gagctcatca | 300 |
| gagaactcac cgcttctcat gccaccaagg tgcagacaca caagccttac ttggtgacct | 360 |
| tcgacctcac agactctggg gccatagttg cagcagcagc tgagatcctg cagtgctttg | 420 |
| gctatgtcga catacttgtc aacaatgctg ggatcagcta ccgtggtacc atcatggaca | 480 |
| ccacagtgga tgtggacaag agggtcatgg agacaaaacta ctttggccca gttgctctaa | 540 |
| cgaaagcact cctgccctcc atgatcaaga ggaggcaagg ccacattgtc gccatcagca | 600 |
| gcatccaggg caagatgagc attcctttc gatcagcata tgcagcctcc aagcacgcaa | 660 |
| cccaggcttt ctttgactgt ctgcgtgccg agatggaaca gtatgaaatt gaggtgaccg | 720 |
| tcatcagccc cggctacatc cacaccaacc tctctgtaaa tgccatcacc gcggatggat | 780 |
| ctaggtatgg agttatggac accaccacag cccagggccg aagccctgtg gaggtggccc | 840 |
| aggatgttct tgctgctgtg gggaagaaga agaaagatgt gatcctggct gacttactgc | 900 |
| cttccttggc tgtttatctt cgaactctgg ctcctgggct cttcttcagc ctcatggcct | 960 |
| ccagggccag aaaagagcgg aaatccaaga actcctagta ctctgaccag ccagggccag | 1020 |
| ggcagagaag cagcactctt aggcttgctt actctacaag ggacagttgc atttgttgag | 1080 |
| actttaatgg agatttgtct cacaagtggg aaagactgaa gaaacacatc tcgtgcagat | 1140 |
| ctgctggcag aggacaatca aaacgacaa caagcttctt cccagggtga ggggaaacac | 1200 |
| ttaaggaata aatatggagc tggggtttaa cactaaaaac tagaaataaa catctcaaac | 1260 |
| agtaaaaaaa aaaaaaaa | 1278 |

<210> SEQ ID NO 26
<211> LENGTH: 1614
<212> TYPE: DNA
<213> ORGANISM: Homo sapiens
<220> FEATURE:
<221> NAME/KEY: misc_feature
<223> OTHER INFORMATION: Incyte ID No.: 1803830CB1

<400> SEQUENCE: 26

| | |
|---|---|
| gttttgggggg tgaaaaggca aaaggcgggt gaaaggctgc ctcccgagac tctccttgct | 60 |
| tggaattctg cccactctgc ggagttagca gtcacgacct ccagcacagg atgtggtacc | 120 |
| acagattgtc ccacctacac agcaggcttc aggacttgct gaagggagga gtcatatatc | 180 |
| cggcccttcc acagcccaac ttcaaaagct tacttccttt agctgtccat ggcaccata | 240 |
| cagcctccaa gtctctgact tgtgcttggc agcaacatga agatcatttt gagctgaaat | 300 |
| atgctaatac cgtgatgcgc cttgattacg tctggcttcg agaccactgc cgctcagcat | 360 |
| cgtgctacaa ctctaagact caccagcgca gctgggatac tgccagtgtg gatttatgta | 420 |
| tcaagccaaa gaccattcgt ctggatgaga ccacactctt tttcacttgg ccagatggtc | 480 |
| atgtgactaa atatgatttg aattggctgg tgaaaaacag ctatgaaggg cagaaacaaa | 540 |
| aagtcatcca gcctagaata ctatggaatg ctgaaatcta ccagcaagcc caagttccat | 600 |
| cggtagattg ccagagcttc ttagaaacca acgagggact gaagaagttt ctgcaaaact | 660 |
| ttctgctcta tggaattgca ttcgtagaaa atgtccctcc cactcaagag cacacagaga | 720 |
| agttggcaga aaggatcagc ttaatcagag aaaccattta tgggaggatg tggtatttca | 780 |
| cttcagactt ctccagaggt gacactgcgt acaccaagct agctctggat cggcacactg | 840 |
| acactaccta ttttcaagag ccctgtgcca ttcaagtgtt tcattgtctt aaacatgaag | 900 |

```
gaactggtgg caggacactg ctagtagatg gattctatgc agcagaacag gtacttcaaa      960
aggcacctga ggaatttgaa ctcctcagta aagtgccatt gaagcatgaa tatattgaag     1020
atgttggaga atgtcacaac cacatgattg ggattgggcc agtcttaaat atctacccat     1080
ggaataaaga gctgtatttg atcaggtaca acaactatga ccgggctgtc atcaataccg     1140
ttccttatga tgtcgtccat cgctggtata cagcacaccg gactctaacg atagagttga     1200
ggagacctga gaatgagttt tgggtcaaac taaagcctgg caggtccta tttatagaca      1260 actggcgtgt cctacatggc agggaatgct tcactggcta ccgccaactg tgtggctgct     1320
atttaacaag agatgatgta ttaaacactg ctcgcctctt ggggcttcag gcttaaaatt     1380
gacagcatct ggattatgaa tacacctggc accctggcta ccagaatttc atatgggcag     1440
aataatattg tgtcaaactc tacttcagat tgtctcctta tcccatccca caaaacagaa     1500
tctgtccgtt tctctagtaa gggagacttg ttggagaggc gggactctga gttatctaat     1560
gtcagacatc tagtggggca gctctcttcc tcgtgttata acatgcatac ccgt           1614
```

<210> SEQ ID NO 27
<211> LENGTH: 3136
<212> TYPE: DNA
<213> ORGANISM: Homo sapiens
<220> FEATURE:
<221> NAME/KEY: misc_feature
<223> OTHER INFORMATION: Incyte ID No.: 1867333CB1

<400> SEQUENCE: 27

```
cgacgccggc gtgatgtggc ttccgctggt gctgctcctg gctgtgctgc tgctggccgt       60
cctctgcaaa gtttacttgg gactattctc tggcagctcc ccgaatcctt tctccgaaga      120
tgtcaaacgg cccccagcgc ccctggtaac tgacaaggag gccaggaaga aggttctcaa      180
acaagctttt tcagccaacc aagtgccgga agctggat gtggtggtaa ttggcagtgg        240
ctttgggggc ctggctgcag ctgcaattct agctaaagct ggcaagcgag tcctggtgct      300
ggaacaacat accaaggcag ggggctgctg tcataccttt ggaaagaatg gccttgaatt      360
tgacacagga atccattaca ttgggcgtat ggaaagggc agcattggcc gttttatctt       420
ggaccagatc actgaagggc agctggactg gctcccctg tcctctcctt ttgacatcat       480
ggtactggaa gggcccaatg gccgaaagga gtacccatg tacagtggag agaaagccta      540
cattcagggc ctcaaggaga gtttccaca ggaggaagct atcattgaca gtatataaa      600 gctggttaag gtggtatcca gtggagcccc tcatgccatc ctgttgaaat tcctcccatt      660
gcccgtggtt cagctcctcg acaggtgtgg gctgctgact cgtttctctc cattccttca      720
agcatccacc cagagcctgg ctgaggtcct gcagcagctg ggggcctcct ctgagctcca      780
ggcagtactc agctacatct tccccactta cggtgtcacc cccaaccaca gtgcctttc      840 catgcacgcc ctgctggtca accactacat gaaaggaggc ttttatcccc gaggggttc      900 cagtgaaatt gccttccaca ccatccctgt gattcagcgg gctggggcg ctgtcctcac     960 aaaggccact gtgcagagtg tgttgctgga ctcagctggg aaagcctgtg tgtcagtgt    1020 gaagaagggg catgagctgg tgaacatcta ttgccccatc gtggtctcca acgcaggact    1080
gttcaacacc tatgaacacc tactgccggg gaacgccgc tgcctgccag tgtgaagca     1140 gcaactgggg acggtgcggc ccggcttagg catgacctct gttttcatct gcctgcgagg    1200
caccaaggaa gacctgcatc tgccgtccac caactactat gtttactatg acacggacat    1260
ggaccaggcg atggagcgct acgtctccat gcccagggaa gaggctgcgg aacacatccc    1320
```

```
tcttctcttc ttcgctttcc catcagccaa agatccgacc tgggaggacc gattcccagg      1380
ccggtccacc atgatcatgc tcatacccac tgcctacgag tggtttgagg agtggcaggc      1440
ggagctgaag ggaaagcggg gcagtgacta tgagaccttc aaaaactcct ttgtggaagc      1500
ctctatgtca gtggtcctga aactgttccc acagctggag gggaaggtgg agagtgtgac      1560
tgcaggatcc ccactcacca accagttcta tctggctgct ccccgaggtg cctgctacgg      1620
ggctgaccat gacctgggcc gcctgcaccc ttgtgtgatg gcctccttga gggcccagag      1680
ccccatcccc aacctctatc tgacaggcca ggatatcttc acctgtggac tggtcggggc      1740
cctgcaaggt gccctgctgt gcagcagcgc catcctgaag cggaacttgt actcagacct      1800
taagaatctt gattctagga tccgggcaca gaagaaaaag aattagttcc atcagggagg      1860
agtcagagga atttgcccaa tggctggggc atctcccttg acttacccat aatgtctttc      1920
tgcattagtt ccttgcacgt ataaagcact ctaatttggt tctgatgcct gaagagaggc      1980
ctagtttaaa tcacaattcc gaatctgggg caatggaatc actgcttcca gctggggcag      2040
gtgagatctt tacgcctttt ataacatgcc atccctacta ataggatatt gacttggata      2100
gcttgatgtc tcatgacgag cggcgctctg catccctcac ccatgcctcc taactcagtg      2160
atcaaagcga atattccatc tgtggataga acccctggca gtgttgtcag ctcaacctgg      2220
tgggttcagt tctgtcctga ggcttctgct ctcattcatt tagtgctacg ctgcacagtt      2280
ctacactgtc aagggaaaag ggagactaat gaggcttaac tcaaaacctg gcatggtttt      2340
tggttgccat tccataggtt tggagagctc tagatctctt ttgtgctggg ttcagtggct      2400 cttcaggga caggaaatgc ctgtgtctgg ccagtgtggt tctggagctt tggggtaaca       2460
gcaggatcca tcagttagta gggtgcatgt cagatgatca tatccaattc atatggaagt      2520
cccgggtctg tcttccttat catcggggtg gcagctggtt ctcaatgtgc cagcagggac      2580
tcagtacctg agcctcaatc aagccttatc caccaaatac acaggaaagg gtgatgcagg      2640
gaagggtgac atcaggagtc agggcatgga ctggtaagat gaatactttg ctgggctgaa      2700
gcaggctgca gggcattcca gccaagggca cagcagggga cagtgcaggg aggtgtgggg      2760
taagggaggg aagtcacatc agaaaaggga agccacggaa atgtgtgtga agcccagaaa      2820
tggcatttgc agttaattag cacatgtgag ggttagacag gtaggtgaat gcaagctcaa      2880
ggtttggaaa aatgactttt cagttatgtc tttggtatca gacatacgaa aggtctcttt      2940
gtagttcgtg ttaatgtaac attaataaat ttattgattc cattgcttta acatttgaaa      3000
tttattttgg tttttgttc aagaaaacaa aactattatt gtgatggcat ttgcagaagc       3060
tcagtaaaac actatatact gaataacacc aaaataagct ttaaaaaaat aaaattaagt      3120
aattataaaa aaaaaa                                                      3136
```

<210> SEQ ID NO 28
<211> LENGTH: 1594
<212> TYPE: DNA
<213> ORGANISM: Homo sapiens
<220> FEATURE:
<221> NAME/KEY: unsure
<222> LOCATION: 1530
<223> OTHER INFORMATION: a or g or c or t, unknown, or other
<220> FEATURE:
<221> NAME/KEY: misc_feature
<223> OTHER INFORMATION: Incyte ID No.: 2906094CB1

<400> SEQUENCE: 28

```
cccacgcgtc cgcggacgcg tgggggcgtt cagactctta gctgaacgcg gactgcggcg        60
```

-continued

| | |
|---|---|
| gctatgctgt ggagcggctg ccggcgtttc ggggcgcgcc tcggctgcct gcccggcggt | 120 |
| ctccgggtcc tcgtccagac cggccaccgg agcttgacct cctgcatcga cccttccatg | 180 |
| ggacttaatg aagagcagaa agaatttcaa aaagtggcct ttgactttgc tgcccgagag | 240 |
| atggctccaa atatggcaga gtgggaccag aaggagctgt tcccagtgga tgtgatgcgg | 300 |
| aaggcagccc agctaggctt cggagggggtc tacatacaaa cagatgtggg cgggtctggg | 360 |
| ctgtcacgtc ttgataccte tgtcattttt gaagccttgg ctacaggctg caccagcacc | 420 |
| acagcctata taagcatcca caacatgtgt gcctggatga ttgatagctt cggaaatgag | 480 |
| gaacagaggc acaaattttg cccaccgctc tgtaccatgg agaagtttgc ttcctactgc | 540 |
| ctcactgaac caggaagtgg gagtgatgct gcctctcttc tgacctccgc taagaaacag | 600 |
| ggagatcatt acatcctcaa tggctccaag gccttcatca gtggtgctgg tgagtcagac | 660 |
| atctatgtgg tcatgtgccg aacaggagga ccaggcccca agggcatctc atgcatagtt | 720 |
| gttgagaagg ggaccccctgg cctcagcttt ggcaagaagg agaaaaaggt ggggtggaac | 780 |
| tcccagccaa cacgagctgt gatcttcgaa gactgtgctg tccctgtggc aacagaatt | 840 |
| gggagcgagg ggcagggctt cctcattgcc gtgagaggac tgaacggagg gaggatcaat | 900 |
| attgcttcct gctccctggg ggctgcccac gcctctgtca tcctcacccg agaccacctc | 960 |
| aatgtccgga agcagtttgg agagcctctg ccagtaacc agtacttgca attcacactg | 1020 |
| gctgatatgg caacaaggct ggtggccgcg cggctgatgg tccgcaatgc agcagtggct | 1080 |
| ctgcaggagg agaggaagga tgcagtggcc ttgtgctcca tggccaagct ctttgctaca | 1140 |
| gatgaatgct ttgccatctg caaccaggcc ttgcagatgc acgggggcta cggctacctg | 1200 |
| aaggattacg ctgttcagca gtacgtgcgg gactccaggg tccaccagat tctagaaggt | 1260 |
| agcaatgaag tgatgaggat actgatctct agaagcctgc ttcaggagta gaacccacac | 1320 |
| ttgttctggc ctggtgttca gtgcgactgc agtcagtgtt gagtggtgcc atgtgggccg | 1380 |
| ctctattcca aaggaatcat ggattagacc caaaggctga gctcctctag ggcaggacct | 1440 |
| gcaccctgtg tgttggcacc agcatcgggt cttggactgg gggcagatcc ccagtggaac | 1500 |
| cggaagagct ggactgatga gaaacatcan ggaagacaca tactacccct ggttttccta | 1560 |
| atgcccagaa gggtgaccag tgaaagattc accc | 1594 |

<210> SEQ ID NO 29
<211> LENGTH: 1338
<212> TYPE: DNA
<213> ORGANISM: Homo sapiens
<220> FEATURE:
<221> NAME/KEY: misc_feature
<223> OTHER INFORMATION: Incyte ID No.: 3294314CB1

<400> SEQUENCE: 29

| | |
|---|---|
| ggtgagcgca gtctgtccga ggcaacaaga tggcagctgc ggagccgtct ccgcggcgcg | 60 |
| tgggcttcgt gggcgcgggc cgcatggcgg gggccatcgc gcaggcctc atcagagcag | 120 |
| gaaaagtgga agctcagcac atactggcca gtgcaccaac agacaggaac ctatgtcact | 180 |
| ttcaagctct gggttgccgg accacgcact ccaaccagga ggtgctgcag agctgcctgc | 240 |
| tcgtcatctt tgccaccaag cctcatgtgc tgccagctgt cctggcagag gtggctcctg | 300 |
| tggtcaccac tgaacacatc ttggtgtccg tggctgctgg ggtgtctctg agcaccctgg | 360 |
| aggagctgct gccccaaac acacgggtgc tgcgggtctt gcccaacctg ccctgtgtgg | 420 |
| tccaggaagg ggccatagtg atggcgcggg ccgccacgt ggggagcagc gagaccaagc | 480 |

-continued

| | |
|---|---|
| tcctgcagca tctgctggag gcctgtgggc ggtgtgagga ggtgcctgaa gcctacgtcg | 540 |
| acatccacac tggcctcagt ggcagtggcg tggccttcgt gtgtgcattc tccgaggccc | 600 |
| tggctgaagg agccgtcaag atgggcatgc ccagcagcct ggcccaccgc atcgctgccc | 660 |
| agaccctgct ggggacggcc aagatgctgc tgcacgaggg ccaacaccca gcccagctgc | 720 |
| gctcagacgt gtgcaccccg ggtggcacca ccatctatgg actccacgcc ctggagcagg | 780 |
| gcgggctgcg agcagccacc atgagcgccg tggaggctgc cacctgccgg gccaaggagc | 840 |
| tcagcagaaa gtaggctggg ctctggccat cctttcctgc ctctgtgccc ctgcctctcc | 900 |
| ctgtgtccct tccctgagg actgcggctc cctcctcct gcatgagggt ctcctactgc | 960 |
| tccttctccc cttgcacagg gaaatgcagg gggcaggact gggaggttc cagcaggcgg | 1020 |
| gggagccccg accagtgggg acactcctcc ctccccagtg agcagaaggc accgtggtgg | 1080 |
| tggctctgcc ccttgctgca gtgagcccac cttgctgcaa cattggttct gagggcccca | 1140 |
| agagatggcg tcttggtcat ttgcccgcat ggttgggcag ttggttgagg ccatgaacag | 1200 |
| aacttacggt aacaggcacg gctggcccaa tgcctggtct ggagctggag cttgcctttg | 1260 |
| gctttccaag tgggctcgtg cagctacagc caggccggct gcctcatctc agctctaggg | 1320 |
| ggcacgagca tatggggt | 1338 |

<210> SEQ ID NO 30
<211> LENGTH: 1091
<212> TYPE: DNA
<213> ORGANISM: Homo sapiens
<220> FEATURE:
<221> NAME/KEY: misc_feature
<223> OTHER INFORMATION: Incyte ID No.: 4940951CB1

<400> SEQUENCE: 30

| | |
|---|---|
| ccagaaggtc accgccatgg ccgcgccctt cttttccact cctttccagc cctacgtcta | 60 |
| ccagagccag caaggatctg tgacggcgtt tcagatatcc ggtggagatg tgcaggtcct | 120 |
| gcaggtgatg ctgaagtctc aggagaagct gactgcaaaa ccaggtgcaa tgtgctacat | 180 |
| gtctgggaat atgcagatgg acaacaatta cttgcctgaa aatgatggag gcgtgtggca | 240 |
| gtggattttt gggaaacgtg taagcagcac cattttcttt aattctggat ctgatgatgg | 300 |
| atatgtcggg attgctgcac catttcctgg gaggatactg ccgtagatc taacaaactt | 360 |
| tagtggagaa cttctttgcc aggcagatgc ttttctatgt tcggtcaatg atgtctccgt | 420 |
| ctctagtaca gttgagccaa ggccacgaa tattgagatt ggtgcagaga tgatccttaa | 480 |
| acaaaaactt aggggccagg ggatggcttt tcttgttggt ggtggatcag tcatgcagaa | 540 |
| aatccttgct cctagagagg tgataactgt tgatgctgct tgtattgtgg ctatgtcggc | 600 |
| caccattaac ttccagttga agagccctaa ccagcttaga agagcagttt tgggggtga | 660 |
| taaccagcta acagcatctc tcacgggacc aggtgttgtt tcattcaaa gtctgccatt | 720 |
| ccatcgactc tcacagagaa tcgccagcag tagatcagtg gcaggcccaa gcttgaggga | 780 |
| caacccaaag ttcttcatcc agattgtcat gttcttcttc ctggcctatg ttatgattgt | 840 |
| atcatccata attctgacag atgtttaagc gattcagtga gcttttggtg tattcctaga | 900 |
| caagttatcg aagagttaaa gctacctccc caatgtttaat gtagatgtaa gagaacgaat | 960 |
| ttcacaagct gttgttagaa accttagcag aaggttcttc attttttttt ctctaacagt | 1020 |
| ttggagggg cggggcgggt ttcttggtta gcgtgtaaag aggaagacag caaaatcaag | 1080 |
| ttgcacagcg a | 1091 |